US007250258B2

(12) United States Patent
Aerssens et al.

(10) Patent No.: US 7,250,258 B2
(45) Date of Patent: Jul. 31, 2007

(54) CDK5 GENETIC MARKERS ASSOCIATED WITH GALANTAMINE RESPONSE

(75) Inventors: Jeroen Aerssens, Nieuwrode (BE); Maria Athanasiou, Derby, CT (US); Carlos Brain, Somerville, MA (US); Nadine Cohen, Warren, NJ (US); Bradley Dain, Hamden, CT (US); R. Rex Denton, Madison, CT (US); Richard S. Judson, Guilford, CT (US); Vural Ozdemir, Long Beach, CA (US); Carol R. Reed, Bethany, CT (US)

(73) Assignee: PGxHealth LLC, New Haven, CT (US)

( * ) Notice: Subject to any disclaimer, the term of this patent is extended or adjusted under 35 U.S.C. 154(b) by 0 days.

(21) Appl. No.: 11/005,029

(22) Filed: Dec. 7, 2004

(65) Prior Publication Data
US 2005/0255494 A1 Nov. 17, 2005

Related U.S. Application Data

(60) Provisional application No. 60/530,000, filed on Dec. 15, 2003.

(51) Int. Cl.
C12Q 1/68 (2006.01)
C12P 19/34 (2006.01)
C07H 21/04 (2006.01)

(52) U.S. Cl. .................. 435/6; 435/91.2; 435/287.2; 536/23.1; 536/23.5

(58) Field of Classification Search .................... None
See application file for complete search history.

(56) References Cited

U.S. PATENT DOCUMENTS

| | | | |
|---|---|---|---|
| 4,663,318 A | 5/1987 | Davis | |
| 5,972,614 A | 10/1999 | Ruano et al. | |
| 6,150,354 A | 11/2000 | Davis et al. | |
| 6,268,358 B1 | 7/2001 | Davis et al. | |
| 6,319,919 B1 | 11/2001 | Davis et al. | |
| 6,323,196 B1 | 11/2001 | Kosley, Jr. et al. | |
| 6,326,196 B1 | 12/2001 | Parker et al. | |
| 6,358,941 B1 | 3/2002 | Snorrason et al. | |
| 6,645,990 B2 * | 11/2003 | Askew et al. | 514/342 |
| 2003/0145343 A1 * | 7/2003 | McNeish et al. | 800/18 |
| 2004/0267458 A1 | 12/2004 | Judson et al. | |
| 2005/0048543 A1 | 3/2005 | Aerssens et al. | |
| 2005/0250118 A1 | 11/2005 | Aerssens et al. | |
| 2005/0260613 A1 | 11/2005 | Aerssens et al. | |
| 2005/0277626 A1 * | 12/2005 | Dinan et al. | 514/214.03 |

FOREIGN PATENT DOCUMENTS

| | | |
|---|---|---|
| EP | 0 236 684 B1 | 5/1992 |
| WO | WO 00/38686 | 7/2000 |
| WO | WO 01/80156 A1 | 10/2001 |

OTHER PUBLICATIONS

Aerssons, J., et al., "APOE genotype and response to galantamine treatment in Alzheimer's disease," *Am. J. Hum. Genet.* 65:A195, Abstract 1067 (1999).
Aerssons, J., et al., "APOE Genotype: No Influence on Galantamine Treatment Efficacy Nor on Rate of Decline in Alzheimer's Disease," *Dement. Geriatr. Cogn. Disord.* 12:69-77, S. Karger (2001).
Bartolucci, C., et al., "Three-dimensional Structure of a Complex of Galanthamine (Nivalin®) with Acetylcholinesterase From *Torpedo californica*: Implications for the Design of New Anti-Alzheimer Drugs," *Proteins* 42:182-191, Wiley-Liss, Inc. (2001).
Coyle, J. and Kershaw, P., "Galantamine, a Cholinesterase Inhibitor that Allosterically Modulates Nicotinic Receptors: Effects on the Course of Alzheimer's Disease," *Biol. Psychiatry* 49:289-299, Elsevier, Inc. (2001).
Farlow, M.R., et al., "Treatment outcome of tacrine therapy depends on apolipoprotein genotype and gender of the subjects with Alzheimer's disease," *Neurology* 50:669-677, Lippincott-Raven Publishers (1998).
Hashiguchi, M., et al., "Truncation of CDK5 Activator p35 Induces Intensive Phosphorylation of Ser202/Thr205 of Human Tau," *J. Biol. Chem.* 277: 44525-44530, American Society for Biochemistry and Molecular Biology (Nov. 2002).
Liu, F., et al., "Involvement of a aberrant glycosylation in phosphorylation of tau by cdk5 and GSK-3β," *FEBS Lett.* 530:209-214, Elsevier Science B.V. (Oct. 2002).
Patrick, G.N., et al., Conversion of p35 to p25 deregulates Cdk5 activity and promotes neurodegeneration, *Nature* 402:615-622, Nature Publishing Group (1999).
Raskind, M.A., et al., "Galantamine in AD A 6-month randomized, placebo-controlled trial with a 6-month extension," *Neurology* 54:2261-2268, Lippincott-Raven Publishers (2000).
Reminyl® (Galantamine HBr) Tablets and Oral Solution, Product Information Sheets, pp. 1-8, Janssen Pharmacetica Products, L.P. (2001).
Rockwood, K., et al., "Effects of a flexible galantamine dose in Alzheimer's disease: a randomised, controlled trial," *J. Neurol. Neurosurg. Psychiatry* 71:589-595, BMJ Publishing Group Ltd. (2001).

(Continued)

*Primary Examiner*—Bradley L. Sisson
(74) *Attorney, Agent, or Firm*—Sterne, Kessler, Goldstein & Fox P.L.L.C.

(57) ABSTRACT

Haplotypes in the CDK5 gene associated with cognitive response to galantamine treatment are disclosed. Compositions and methods for detecting and using these CDK5 haplotypes in a variety of clinical applications are disclosed. Such applications include articles of manufacture comprising galantamine or derivatives thereof that are approved for treating patients having one of these CDK5 haplotypes, methods and kits for predicting the response of an individual to galantamine based upon his/her haplotype profile, and methods for treating Alzheimer's patients based upon their haplotype profile.

26 Claims, 3 Drawing Sheets

OTHER PUBLICATIONS

Rosen, W.G., et al., "A New Rating Scale for Alzheimer's Disease," *Am. J. Psychiatry 141*:1356-1364, American Psychiatric Publishing, Inc. (1984).

Samochocki, M., et al., "Galantamine is an allosterically potentiating ligand of the human α4/β2 nAChR," *Acta Neurol Scand. 176*(Supp):68-73, Munksgaard International Publishers Ltd. (2000).

Scott, L.J. and Goa, K.L., "Galantamine: A Review of its Use in Alzheimer's Disease," *Drugs 60*:1095-1122, Adis International Ltd. (2000).

Storch, A., et al., "Physostigmine, galanthamine and codeine act as 'noncompetitive nicotinic receptor agonists' on clonal rat pheochromocytoma cells," *Eur. J. Pharmacol. Mol. Pharmacol. Sec. 290*:207-219, Elsevier Science B.V.(1995).

Tariot, P.N., et al., "A 5-month, randomized, placebo-controlled trial of galantamine in AD," *Neurology 54*:2269-2276, Lippincott-Raven Publishers (2000).

Tseng, H-C., et al., "A survey of Cdk5 activator p35 and p25 levels in Alzheimer's disease brains," *FEBS Lett. 523*:58-62, Elsevier Science B.V. (Jul. 2002).

Wilcock, G.K., et al., "Efficacy and safety of galantamine in patients with mild to moderate Alzheimer's disease: multicentre randomised controlled trial," *BMJ 321*:1-7, BMJ Publishing Group Ltd. (2000).

Zheng, Y-I., et al., "A peptide derived from cyclin-dependent kinase activator (p35) specifically inhibits Cdk5 activity and phosphorylation of tau protein in transfected cells," *Eur. J. Biochem. 269*:4427-4434, The Federation of European Biochemical Societies and Blackwell Publishing (Sep. 2002).

\* cited by examiner

POLYMORPHISMS IN THE CDK5 GENE

```
CCGTCCCCG CCACCACCTC TCGCCTACCG CTCGCTCTGG ACTTCGTGCC
CGGGGTCTCG GGGTCTCTCC CCGTCCTCCG GCGCACTCGC GCGCTCCCGA  100
CGACTGCCCC GTGCCCACCC CGGGGCGCGC CCCCGCCGCT CCCAACTTCT
CCCAACTCAA CTTTCCCCCG CGCCGCGGGC AGGCCAGCCC CCTGCGTGCG  200
CGCCCCCCGG CGCACCGTGC GCGGTCCCGC CTTCGCGGGT GGGGAGGCGG
GAGCGGGGGC CGGGGCGGGG GCGCGCTTCC AGGCACAGCC CGGCACCAGG  300
GGCCGCCCCC GCCGTCCCTC TGCCCCAAGC TTCTCCACTC GGGGCTCGGG
AGCCCCGAGG ATGCCGTCCC TTGGCTCCAT TACGGCACCT CTGAGTGTAA  400
AGGAGCCCTT CTCACGCTAG GGATCCCAGG CAGCAAAACG CAGGCACAAG
GAAATTCGGG GAAGTCGAAA CATAAACGTA TCGGGGTTGA GATTCTCTTG  500
CCCCCCTCAA TAACCCCCGT GCCTCCAAGA AAGCCCCTGA GGGACGGGTG
GCGAGTGGGT GAGAAGGGTG ACAGGGGCTG GAGGCTGGCC GCCCGGTACC  600
CTGAGCTGAT CTGGGAGAGG GTAACTTGTT AGAGGCTCTC CACTTCCAGA
GAGGGACAGA GATTCGCTGT GCTGGCCTCC TTCCTCTTGA ATGGAACCTC  700
CACACTGAAC CGAACCCTAG GCAGAGCCAT CACTTATCAT TCAAGACCTT
TGTGTGTAGT TCTTTTTTGC CCAACGAAAT CACAAAGTCT TCCAGATAAG  800
GAATACACTT TTTGCTTCTT TTCCCTTGTG TATGCAAAAG CATTCAGATA
GAAACGAGTT AATTAACACG TGTTTAGCAG CAACTCTGGT TCCGGTGCTG  900
AGGAGTGCTG TTTGGGATCC TTTTCCCTCG GTCCATAGCC CTCAAGAATG
CAATCATGAG ACAATTAGAG AGGCAGCGTA AGGGAATCTA TAATCAGCTC 1000
CTTTAAGGGG TGAGGCAGAG GCTGCTGCAA GTTGAGCATC GGTCTGTGGT
CTTGTCTGTG GAGGGGGTTA ACCAACCTGC CTGCCACACC CTGGCTGACT 1100
CCAGTGGGCC CTGTTCCGGA GACTGGGGTC TGAGGGGGAC CCCCAGGGCT
CCACCCAGTT TTCCTCAGCA TGTCAGAGTT CAGCGGCTAG AGTCGGGTGG 1200
GCTCCGAGAC AACAAACGGG GCTCAGCAGA GAGGGGGTCT TTGGCGTGTG
TCCCTCCACT AAAATCCAGC CTCGAAGGGG CACAGCTGTT CTCCCAGCCC 1300
TGCGGTCAGC TGTTCCCTGT GAGGTCATCA TCGCTCACAG GCATTCCCCA
GTCAATTCTG GGGTCACTAG GTGGCTTGGG GAGAGGTGGA AACCCGTGCT 1400
GAGGTCGTCA AGAGGCCGTT GGGAACACAA TGCCACCAAC CAGGTCAGCG
CTGGGCCGCC AGTGCCCGGG ATCTAGGCCG CCAAACCCCA AACCCCTAAC 1500
CGAGAGCGCT CCGCCCCCAT TTCCGCTGCA TTCTGGAACG CGTAGTCCCG
GAGCGGCCCT TTTCAAGAGG GCTGGGAGCA CATAAAAGGA ATAACAACAG 1600
CGGGGCACAC TGGGAACCAC GGCGCCGCGG CGGGGCGCCC GGAAAACGGA
CACGCGTTGC TTCCTGGGAC TTGAAGTCCA AGGTTTGCCT CCGCGGTAGA 1700
                                             G
AACGGAGCCC TGGAGTCGAG TGCTGCAGAG AGCGTGAGCG CAGACGGCTG
GGGGTTGTAG TCTTCTTGTC CTCGGTCTCG GGCATTGCGG GGAGACCTAG 1800
TCGTTTTAGG ACTACAAGCC CCAGAAGGCC CTGCGCGGGC AGACGGGGCG
GGGCTGGAGG CTCAGGTGCC GCCTCCTCTG CAACGCCGGG GCCAGAGTCT 1900
TAAAACCGAG GGCCCGCAGG GGTCCCCCGG CCGCCGCGAT GCAGAAATAC
[EXON 1: 1939..
GAGAAACTGG AAAAGATTGG GGAAGGTAAT GGAATCTCGA GATGTTCCTG 2000
.. 1975]
CAAGAGCTCC TCTGCAGATC CTTCGGCATT CCTTGAAGCC CTGGCTCCCT
TACCGTCAGC AATGCCTACA GGCTCCGATC TCAGCAGCGG CTGCAGCCCT 2100
GGCCCCCTAG CTCAGCACTC CGTGCAGACA CCAGTCTTCC CCGTGTTAGC
ATTTCCCGCA GGGCTCTCAC TCCAACCTTA GCGTTCCCAG TAGACCCGAC 2200
CTCCCAACCG CGACACTTCC TGAAATTTCT CACCCCAGCC TCAGCAGCAC
TTGGACAACC TCACCCCGAC CCCAGCCTC GTTTCTTGCT GCAGACCTCC 2300
AACCTCAATA TTTCTGCAGC CCCTCAGTCC TCTCCCAGAC CCCTCCTCAC
TATTTCCAGA CCCTTCCGGA GCACCGCCTT CATTTTAGAC ATCCTTGCCC 2400
TGGCAACCGC ACTCGCCCCT CCTGCCGAGC CCCTGGAGCC TCGGTGGGCA
CCTTCTCCTC CCTCCCACC TGCCACATCC TCACTCACAA AGCTCACCAA 2500
CCTACCTTCA CCCTGAATCC CTTCCCTTGC ATACTGAGAC GCTGCCTTCA
CCTCTCTCAG GAGGCATTTC CTGGCTTAGG GAAGAGTGCC GCATCCTCAC 2600
CCTGACCCCT GACCTCCTTC CCCTAGGCAC CTACGGAACT GTGTTCAAGG
[EXON 2: 2627..
CCAAAAACCG GGAGACTCAT GAGATCGTGG CTCTGAAACG GGTGAGGCTG 2700
```

FIGURE 1A

```
             GATGACGATG ATGAGGTAGG ACTGGGGAGT GGGATACGGC CTGGGGAGGG
.. 2715]
GTTTGAGGGC CTGGGCTGGG TGGGATCTGA CTGCTGCCCA CCGGCCCCCT 2800
CACATATGCA GGGTGTGCCG AGTTCCGCCC TCCGGGAGAT CTGCCTACTC
[EXON 3: 2812..
AAGGAGCTGA AGCACAAGAA CATCGTCAGG TGTGCGGGAG GCGGGTGCTC 2900
.. 2879]
CTTGCCGGTG TGGCCGCTTG GGGGAGGCGG GGGCTGACAC TGGACGTCTG
TCAGGCGGAC CTGCCTGGCT GAGCCCTTCT TTTGCCCTAG GCTTCATGAC 3000
[EXON 4: 2991..
GTCCTGCACA GCGACAAGAA GCTGACTTTG GTTTTTGAAT TCTGTGACCA
GGTGAAAGGC GGGGTTTGGA GGACAGTAGC CTTGGGAAGG TATAGGGGCC 3100
.. 3051]
CAGATTGAGG TTAAACTCTG TCCCATTCCC CCACTCATAT CCCTTTTCAG
GACCTGAAGA AGTATTTTGA CAGTTGCAAT GGTGACCTCG ATCCTGAGAT 3200
[EXON 5: 3151..
TGTAAAGGTG AGGAGAGTGG TGTTGGGGGA CCCCTCAGGC TGGGGTCGGA
.. 3207]
GTCTGCATTC GGTGTAAGCA CCCCTTGGGC TCTAAGTTTG GGCCCTGAAC 3300
AGGGACACTC TAGGGTGTTA GAGAATGAGA AAACCCTGTT TCTGTCCTCC
AGGGGTCTCC AGTCTTAGTG AGCATTTTCA CGTGGTCATC TTTGACCCGC 3400
ACAGTGTCAT TCTGATGTCA GTGATATTAT TTACACTCGA GAGATGAGAA
AATGAGGTTC AAGGAGATAC ACTCATTCAT TCAACACATA CTTACTGAAT 3500
GCTTCACTGT GTGCCAGGTG CTTTTCTAGG CCCAAGACCA AATGCCTTGG
TCCAGGTTCC AGGGGAGCCA GTCCTGAATG ATACTACAGC ACGATATTTA 3600
TGTTGATGTT CACGGCGTGC ATACTCAGAT GCGGCCAGGA AGGGAAGATC
AGCATGGGCT GGGATCTAGG CCGGATCTAG GATCCACCTG CCAAGGCCCA 3700
TTAGGCTGTA TGGTCCAGGA AGGTGGGGAC CAGAGCCAGC TTCTTTACTT
TGGTCCCTCT AATGCCTAGC ACAGTATAAA GCAGGTCCTG GATGGCGAAT 3800
GAATGGTGTC ACTCTGAACC AGGTGCTGAA AGGTGGGTGG GGTGGAGCGA
AGCACAGGGT GAGGAGAGGA GCCGACCCGT TGCTGGGCAC AGTTGCATGT 3900
                                                  C
TCAGGGCGTC TGACTCCCTT CTCCCTCTCT CCTCCCAGTC ATTCCTCTTC
[EXON 6: 3939..
CAGCTACTAA AAGGGCTGGG ATTCTGTCAT AGCCGCAATG TGCTACACAG 4000
GGACCTGAAG CCCCAGAACC TGCTAATAAA CAGGGTACTT CTTGGGAAGA
.. 4034]
AGGTGGGGAA TGGAGAGGCT GGGGCCAGGG CACGGGGAGC ACAGAGGGAA 4100
GAGGACTGGG AGGATGGAGT TGGTGCTGTC CCAAGGCTTT TTAAAGGCCC
TTCTCCATGT CCCCTTCCCA TTCCCTTCAG AATGGGGAGC TGAAATTGGC 4200
[EXON 7: 4181..
TGATTTTGGC CTGGCTCGAG CCTTTGGGAT TCCCGTCCGC TGTTACTCAG
CTGAGGTGAG CTAGAAGATG GGATATGGGA TTGGGGAGG GAGTCCCTCA 4300
.. 4255]
GCTCCAACCC CAGGACCCAA AACATTATTT TCCTCTCCTC TCTGAGCCTC
CTCCTCAAAC CTCCTCCCCA GTCCTCTAAG TGGGAGGTCC CTTTCGGGGG 4400
GGGTCTCCTC CAGGTGGTCA CACTGTGGTA CCGCCCACCG GATGTCCTCT
[EXON 8: 4414..
TTGGGGCCAA GCTGTACTCC ACGTCCATCG ACATGTGGTC AGCCGGCTGC 4500
ATCTTTGCAG GTGATGTGCT GGGGTGTTGC AGAGGCACCT TCTTTCCCAT
.. 4510]
TTGAGTTGAC AAATAGGGTC TGGAGGGTCC CCTCTGGGGG AAGGGAGGGA 4600
GGCCCTGGGA CTGGAGCTGG AAGGTCAGGG GGTACCTCAG AGTGAGGGGT
CCTTCACATG TCACATCTTA GCCCCCTGTC TATCCCCCAG AGCTGGCCAA 4700
[EXON 9: 4691..
TGCTGGGCGG CCTCTTTTTC CCGGCAATGA TGTCGATGAC CAGTTGAAGA
GGATCTTCCG ATATCCTTGC TTTCCTCTGC CTTGAGCCCT CTGGGAGGGG 4800
.. 4761]
AGAGTCCATG GAGTTTTGAG CACAATGGGT GAGGGCAGTG ATGGTGTGGG
          G
GTAGGGTGAT GGGGTCTGTA GGGCTTCTCC TGAGGGCAAG GGGAGAGAGC 4900
```

FIGURE 1B

```
AGGGGTGCTG GACACCCTGA TTGTCACAGT GCAAATGCAC ACTGGAGAAG
GTGTGGCTTG GAGACAGGCA GCGTGCCCTG AGGGGTGAAG CCGAGAGGGT 5000
GTCCCTCCAG GTGAGAGATG GATGCCAGGA TGAAGGAGCC AAAGAGAACA
GGACACATTT TGTGGGAGCA GGGCAAGGAC TGTTTCATTA GGACTAGGAC 5100
AGCAGCATGT GGGTTAGGTG ATTGTCATGG GAAACGTGGC TGGATATGCG
AGTGACCTGC CTGGGGCTGC TTCTGTCAAG CTCAAGCCGG AGGGTAAAGG 5200
GAGGGTGAGA AGTGGGCGGT GGGTATGAGG AATCCCTCCC CAGGAGGGGA
AGAGGCCCTC ACCCTGCCCC TGAAGATGCA GCTGTGGCCC TTTCCCAAGT 5300
                                         T
GATCCTTGAC TCCGTGGACA CACTGCTGGG GACGCCCACC GAGGAGCAGT
[EXON 10: 5323..
GGCCCTCTAT GACCAAGCTG CCAGACTATA AGGTGTGATG GGGAATGTGG 5400
.. 5382]
GGGTCATGGT TCATCAGGGT CACTCGTTTC ACATTCCTAG CGCCTCCATC
CCCCTCCCCC TACCTCTAGT CTGACCCTCC CTGCCTCTCC ACAGCCCTAT 5500
[EXON 11: 5495..
CCGATGTACC CGGCCACAAC ATCCCTGGTG AACGTCGTGC CCAAACTCAA
TGCCACAGGG AGGGATCTGC TGCAGGTAGG TGACCAGGGG TAGAGGGTGG 5600
.. 5575]
GTCAGGACAC TTGCCCAGTG GGACTACAGG AAGGCAGGGC TCTGGGCAGT
GACCTGTCCT GAACCTGCCA CCTCCTTTCC CCCATCTCCA GAACCTTCTG 5700
[EXON 12: 5692..
AAGTGTAACC CTGTCCAGCG TATCTCAGCA GAAGAGGCCC TGCAGCACCC
CTACTTCTCC GACTTCTGTC CGCCCTAGGC CCCGGGACCC CCGCCTCCAG 5800
.. 5778]
GCTGGGCCTG GCCTATTTAA GCCCCCTCTT GAGAGGGTGA GACAGTGGGG
GTGCCTGGTG CGCTGTGCTC CAGCAGTGCT GGGCCCAGCC GGGGTGGGGT 5900
GCCTGAGCCC GAATTTCTCA CTCCCTTTGT GGACTTTATT TAATTTCATA
AATTGGCTCC TTTCCCACAG TCTGGTTGAT GTGGTGGTCA AGTGGCTCTA 6000
CAGGGCCCAT GGGCTGGAGG TGTCTCTGGT CTGTTACTGC CGGCCGCAAT
CCTGCTTCTG GCTCAAAGAC AGCACCTTGC TCTTCTACTT TAAGAGGCCA 6100
TGACCCTCAC CCCTCACCCC TGGGGCAGGG CAGCACTGTC GCTGCACACC
CCTTCCTCCC ACCCTCCCTT CCTCTGCCCA GGAGGGCCTG ATGTGGTCCC 6200
TCAGAGTGAG GGGAGCAAGG ATGGGCTCCC CACCAGGGTG GAGAGGAAAG
GGCTGGGCCT CTCCTTGTGG TTCTCCATAT CTCAGGTGGA TCCTCTTGTC 6300
CTTTCCCTCA TCATCCCCCC CATACCAAGG CCTGCAGGCT GGCACAGGAG
AGCCCCAAAG ATATGGTTCC ATCAGGAACA CCCCCTCCCA CTCCCTATTT 6400
GTCAGTTTCC CAATGTTTGG GGTCCAGTGA AAGAGAGGGA AGTTGGGCCT
GTGGCTGGGG CCTGGTGTGT CCTTACTGGC AGGAAGAGGA AGGGAGGGCT 6500
CCGCCTACCC CCACCCCCAC CCCCACCGTC TCAAGCCTGG GGCCTTTAGC
TCTTGTGGGG AGGCTGAGGA GGCAGAACTT GTTTGTATGG AGACAGGCTG 6600
TGTGCCGCAC TTGGTCCCAA ATGTGGGAAA GGAGTCAGGA TGTAAGGCAG
GACACAGGTG TTCTTGAAAG TGGAGTCACC CCGTCTTCTC CCTGCCTCTT 6700
CTTGCTGAGC TCTGGGCAGA GTTTTCTTCC AGTTATACCT TTATTGCTGA
CTGTGATTCT GCACCTCACA CCTAACCCGG GCTTGGAGGA TACCTGTCCT 6800
CCCTTCTCTC TAAGATGTCA GTCGGCTAAA CTCACTCACA CTGAGGTGCA
AATGACTGAT AACCTCTTGC TACCATTCTC CCCTAGAGAT           6890
```

FIGURE 1C

SEQUENCE LISTING

```
<160> NUMBER OF SEQ ID NOS: 29

<210> SEQ ID NO 1
<211> LENGTH: 6890
<212> TYPE: DNA
<213> ORGANISM: Homo sapiens
<220> FEATURE:
<221> NAME/KEY: misc_feature
<222> LOCATION: (1670)..(1670)
<223> OTHER INFORMATION: n is 'c' or 'g'
<220> FEATURE:
<221> NAME/KEY: misc_feature
<222> LOCATION: (3892)..(3892)
<223> OTHER INFORMATION: n is 'g' or 'c'
<220> FEATURE:
<221> NAME/KEY: misc_feature
<222> LOCATION: (4808)..(4808)
<223> OTHER INFORMATION: n is 'a' or 'g'
<220> FEATURE:
<221> NAME/KEY: misc_feature
<222> LOCATION: (5284)..(5284)
<223> OTHER INFORMATION: n is 'g' or 't'

<400> SEQUENCE: 1
ccgtccccCg ccaccacctc tcgcctaccg ctcgctctgg acttcgtgcc cggggtctcg      60
gggtctctcc ccgtcctccg gcgcactcgc gcgctcccga cgactgcccc gtgcccaccc     120
cggggcgcgc ccccgccgct cccaacttct cccaactcaa ctttccccCg cgccgcgggc     180
aggccagccc cctgcgtgcg cgccccccgg cgcaccgtgc gcggtcccgc cttcgcgggt     240
ggggaggcgg gagcggggggc cggggcgggg gcgcgcttcc aggcacagcc cggcaccagg    300
ggccgccccc gccgtccctc tgccccaagc ttctccactc ggggctcggg agccccgagg    360
atgccgtccc ttggctccat tacggcacct ctgagtgtaa aggagcccct ctcacgctag    420
ggatcccagg cagcaaaacg caggcacaag gaaattcggg gaagtcgaaa cataaacgta    480
tcggggttga gattctcttg ccccccctcaa taaccCccgt gcctccaaga aagccctga    540 gggacgggtg gcgagtgggt gagaagggtg acagggggctg gaggctggcc gcccggtacc    600
ctgagctgat ctgggagagg gtaacttgtt agaggctctc cacttccaga gagggacaga    660
gattcgctgt gctggcctcc ttcctcttga atggaacctc cacactgaac cgaaccctag    720
gcagagccat cacttatcat tcaagaccct tgtgtgtagt tcttttttgc ccaacgaaat    780
cacaaagtct tccagataag gaatacactt tttgcttctt ttcccttgtg tatgcaaaag    840
cattcagata gaaacgagtt aattaacacg tgtttagcag caactctggt tccggtgctg    900
aggagtgctg tttgggatcc tttttccctcg gtccatagcc ctcaagaatg caatcatgag    960
acaattagag aggcagcgta agggaatcta taatcagctc ctttaagggg tgaggcagag   1020
gctgctgcaa gttgagcatc ggtctgtggt cttgtctgtg gagggggtta accaacctgc   1080
ctgccacacc ctggctgact ccagtgggcc ctgttccgga gactggggtc tgaggggac   1140 ccccagggct ccacccagtt ttcctcagca tgtcagagtt cagcggctag agtcgggtgg   1200
```

```
gctccgagac aacaaacggg gctcagcaga gaggggtct ttggcgtgtg tccctccact      1260
aaaatccagc ctcgaagggg cacagctgtt ctcccagccc tgcggtcagc tgttccctgt    1320
gaggtcatca tcgctcacag gcattcccca gtcaattctg gggtcactag gtggcttggg    1380
gagaggtgga aacccgtgct gaggtcgtca agaggccgtt gggaacacaa tgccaccaac    1440
caggtcagcg ctgggccgcc agtgcccggg atctaggccg ccaaaccccca aaccctaac    1500
cgagagcgct ccgcccccat ttccgctgca ttctggaacg cgtagtcccg gagcggccct    1560
tttcaagagg gctgggagca cataaaagga ataacaacag cggggcacac tgggaaccac    1620
ggcgccgcgg cggggcgccc ggaaaacgga cacgcgttgc ttcctgggan ttgaagtcca    1680
aggtttgcct ccgcggtaga aacggagccc tggagtcgag tgctgcagag agcgtgagcg    1740
cagacggctg ggggttgtag tcttcttgtc ctcggtctcg ggcattgcgg ggagacctag    1800
tcgtttagg actacaagcc ccagaaggcc ctgcgcgggc agacggggcg gggctggagg     1860
ctcaggtgcc gcctcctctg caacgccggg gccagagtct taaaaccgag ggcccgcagg    1920
ggtccccgg ccgccgcgat gcagaaatac gagaaactgg aaaagattgg ggaaggtaat     1980
ggaatctcga gatgttcctg caagagctcc tctgcagatc cttcggcatt ccttgaagcc    2040
ctggctccct taccgtcagc aatgcctaca ggctccgatc tcagcagcgg ctgcagccct    2100
ggcccccctag ctcagcactc cgtgcagaca ccagtcttcc ccgtgttagc atttcccgca   2160
gggctctcac tccaacctta gcgttcccag tagacccgac ctcccaaccg cgacacttcc    2220
tgaaatttct caccccagcc tcagcagcac ttggacaacc tcaccccgac ccccagcctc    2280
gtttcttgct gcagacctcc aacctcaata tttctgcagc ccctcagtcc tctcccagac    2340
ccctcctcac tatttccaga cccttccgga gcaccgcctt cattttagac atccttgccc    2400
tggcaaccgc actcgcccct cctgccgagc ccctggagcc tcggtgggca ccttctcctc    2460
cctcccacc tgccacatcc tcactcacaa agctcaccaa cctaccttca ccctgaatcc      2520
cttcccttgc atactgagac gctgccttca cctctctcag gaggcatttc ctggcttagg    2580
gaagagtgcc gcatcctcac cctgacccct gacctccttc ccctaggcac ctacggaact    2640
gtgttcaagg ccaaaaaccg ggagactcat gagatcgtgg ctctgaaacg ggtgaggctg    2700
gatgacgatg atgaggtagg actggggagt gggatacggc ctggggaggg gtttgagggc    2760
ctgggctggg tgggatctga ctgctgccca ccggccccct cacatatgca gggtgtgccg    2820
agttccgccc tccgggagat ctgcctactc aaggagctga agcacaagaa catcgtcagg    2880
tgtgcgggag gcgggtgctc cttgccggtg tggccgcttg ggggaggcgg gggctgacac    2940
tggacgtctg tcaggcggac ctgcctggct gagcccttct tttgccctag gcttcatgac    3000
gtcctgcaca gcgacaagaa gctgactttg gtttttgaat tctgtgacca ggtgaaaggc    3060
ggggtttgga ggacagtagc cttgggaagg tatagggggcc cagattgagg ttaaactctg   3120
tcccattccc ccactcatat ccccttttcag gacctgaaga agtattttga cagttgcaat   3180
ggtgacctcg atcctgagat tgtaaaggtg aggagagtgg tgttggggga cccctcaggc   3240
tggggtcgga gtctgcattc ggtgtaagca ccccttgggc tctaagtttg ggccctgaac    3300
agggacactc tagggtgtta gagaatgaga aaaccctgtt tctgtcctcc agggggtctcc   3360
agtcttagtg agcattttca cgtggtcatc tttgaccccgc acagtgtcat tctgatgtca  3420
gtgatattat ttacactcga gagatgagaa aatgaggttc aaggagatac actcattcat   3480
tcaacacata cttactgaat gcttcactgt gtgccaggtg cttttctagg cccaagacca   3540
aatgccttgg tccaggttcc aggggagcca gtcctgaatg atactacagc acgatattta   3600
```

-continued

```
tgttgatgtt cacggcgtgc atactcagat gcggccagga agggaagatc agcatgggct      3660
gggatctagg ccgatctag gatccacctg ccaaggccca ttaggctgta tggtccagga       3720
aggtggggac cagagccagc ttctttactt tggtccctct aatgcctagc acagtataaa      3780
gcaggtcctg gatggcgaat gaatggtgtc actctgaacc aggtgctgaa aggtgggtgg     3840
ggtggagcga agcacagggt gaggagagga gccgacccgt tgctgggcac anttgcatgt     3900
tcagggcgtc tgactccctt ctccctctct cctcccagtc attcctcttc cagctactaa    3960
aagggctggg attctgtcat agccgcaatg tgctacacag ggacctgaag ccccagaacc    4020
tgctaataaa cagggtactt cttgggaaga aggtggggaa tggagaggct ggggccaggg    4080
cacggggagc acagagggaa gaggactggg aggatggagt tggtgctgtc ccaaggcttt    4140
ttaaaggccc ttctccatgt cccttccca ttcccttcag aatggggagc tgaaattggc     4200
tgattttggc ctggctcgag cctttgggat tcccgtccgc tgttactcag ctgaggtgag    4260
ctagaagatg ggatatggga ttggggaggg gagtccctca gctccaaccc caggacccaa    4320
aacattattt tcctctcctc tctgagcctc ctcctcaaac ctcctcccca gtcctctaag    4380
tgggaggtcc ctttcggggg gggtctcctc caggtggtca cactgtggta ccgcccaccg    4440
gatgtcctct tgggggccaa gctgtactcc acgtccatcg acatgtggtc agccggctgc    4500
atctttgcag gtgatgtgct ggggtgttgc agaggcacct tctttcccat ttgagttgac    4560
aaatagggtc tggaggtgtcc cctctggggg aaggggaggga ggccctggga ctggagctgg  4620 aagtcaggg ggtacctcag agtgagggt ccttcacatg tcacatctta gcccctgtc      4680 tatcccccag agctggccaa tgctgggcgg cctctttttc ccggcaatga tgtcgatgac    4740
cagttgaaga ggatcttccg atatccttgc tttcctctgc cttgagccct ctgggagggg    4800
agagtccntg gagttttgag cacaatgggt gagggcagtg atggtgtggg gtagggtgat    4860
ggggtctgta gggcttctcc tgagggcaag gggagagagc aggggtgctg gacaccctga    4920
ttgtcacagt gcaaatgcac actggagaag gtgtggcttg gagacaggca gcgtgccctg   4980 agggtgaag ccgagagggt gtccctccag gtgagagatg gatgccagga tgaaggagcc    5040
aaagagaaca ggacacattt tgtgggagca gggcaaggac tgtttcatta ggactaggac    5100
agcagcatgt gggttaggtg attgtcatgg gaaacgtggc tggatatgcg agtgacctgc    5160
ctggggctgc ttctgtcaag ctcaagccgg agggtaaagg gagggtgaga agtgggcggt    5220
gggtatgagg aatccctccc caggagggga agaggccctc accctgcccc tgaagatgca    5280
gctntggccc tttcccaagt gatccttgac tccgtggaca cactgctggg gacgcccacc    5340
gaggagcagt ggccctctat gaccaagctg ccagactata agtgtgatg gggaatgtgg    5400 gggtcatggt tcatcagggt cactcgtttc acattcctag cgcctccatc cccctcccc    5460 tacctctagt ctgaccctcc ctgcctctcc acagccctat ccgatgtacc cggccacaac   5520
atccctggtg aacgtcgtgc ccaaactcaa tgccacaggg agggatctgc tgcaggtagg    5580
tgaccagggg tagaggtgg gtcaggacac ttgcccagtg ggactacagg aaggcagggc    5640
tctgggcagt gacctgtcct gaacctgcca cctcctttcc cccatctcca gaaccttctg    5700
aagtgtaacc ctgtccagcg tatctcagca gaagaggccc tgcagcaccc ctacttctcc    5760
gacttctgtc cgccctaggc cccgggaccc ccgcctccag gctgggcctg gcctatttaa    5820 gcccctctt gagagggtga gacagtgggg gtgcctggtg cgctgtgctc cagcagtgct    5880
gggcccagcc ggggtggggt gcctgagccc gaatttctca ctcccttgtg ggactttatt    5940
```

-continued

```
taatttcata aattggctcc tttcccacag tctggttgat gtggtggtca agtggctcta    6000
cagggcccat gggctggagg tgtctctggt ctgttactgc cggccgcaat cctgcttctg    6060
gctcaaagac agcaccttgc tcttctactt taagaggcca tgaccctcac ccctcacccc    6120
tggggcaggg cagcactgtc gctgcacacc ccttcctccc accctcccTT cctctgccca    6180
ggagggcctg atgtggtccc tcagagtgag gggagcaagg atgggctccc caccagggtg    6240
gagaggaaag ggctgggcct ctccttgtgg ttctccatat ctcaggtgga tcctcttgtc    6300
ctttccctca tcatcccccc cataccaagg cctgcaggct ggcacaggag agccccaaag    6360
atatggttcc atcaggaaca cccccctccca ctccctattt gtcagtttcc caatgtttgg    6420
ggtccagtga aagagaggga agttgggcct gtggctgggg cctggtgtgt ccttactggc    6480
aggaagagga agggagggct ccgcctaccc caccccccac ccccaccgtc tcaagcctgg    6540
ggcctttagc tcttgtgggg aggctgagga ggcagaactt gtttgtatgg agacaggctg    6600
tgtgccgcac ttggtcccaa atgtgggaaa ggagtcagga tgtaaggcag gacacaggtg    6660
ttcttgaaag tggagtcacc ccgtcttctc cctgcctctt cttgctgagc tctgggcaga    6720
gttttcttcc agttatacct ttattgctga ctgtgattct gcacctcaca cctaacccgg    6780
gcttggagga tacctgtcct cccttctctc taagatgtca gtcggctaaa ctcactcaca    6840
ctgaggtgca aatgactgat aacctcttgc taccattctc ccctagagat              6890

<210> SEQ ID NO 2
<211> LENGTH: 15
<212> TYPE: DNA
<213> ORGANISM: Artificial Sequence
<220> FEATURE:
<223> OTHER INFORMATION: ASO Probe for Detecting Alleles at PSs in
      Haplotypes Comprising Preferred Embodiments of Response Markers I
      and Response Markers II
<220> FEATURE:
<221> NAME/KEY: misc_feature
<222> LOCATION: (8)..(8)
<223> OTHER INFORMATION: s is 'g' or 'c'

<400> SEQUENCE: 2
gggcacastt gcatg                                                     15

<210> SEQ ID NO 3
<211> LENGTH: 15
<212> TYPE: DNA
<213> ORGANISM: Artificial Sequence
<220> FEATURE:
<223> OTHER INFORMATION: ASO Probe for Detecting Alleles at PSs in
      Haplotypes Comprising Preferred Embodiments of Response Markers I
      and Response Markers II
<220> FEATURE:
<221> NAME/KEY: misc_feature
<222> LOCATION: (8)..(8)
<223> OTHER INFORMATION: r is 'g' or 'a'

<400> SEQUENCE: 3
agagtccrtg gagtt                                                     15

<210> SEQ ID NO 4
<211> LENGTH: 15
<212> TYPE: DNA
<213> ORGANISM: Artificial Sequence
<220> FEATURE:
<223> OTHER INFORMATION: ASO Probe for Detecting Alleles at PSs in
      Haplotypes Comprising Preferred Embodiments of Response Markers I
      and Response Markers II
<220> FEATURE:
<221> NAME/KEY: misc_feature
```

```
<222> LOCATION: (8)..(8)
<223> OTHER INFORMATION: k is 'g' or 't/u'

<400> SEQUENCE: 4
tgcagctktg gccct                                                15

<210> SEQ ID NO 5
<211> LENGTH: 15
<212> TYPE: DNA
<213> ORGANISM: Artificial Sequence
<220> FEATURE:
<223> OTHER INFORMATION: ASO Forward Primer for Detecting Allele
      at PSs in Haplotypes Comprising Preferred Embodiments of Respons
      Markers I and Response Markers II
<220> FEATURE:
<221> NAME/KEY: misc_feature
<222> LOCATION: (14)..(14)
<223> OTHER INFORMATION: s is 'g' or 'c'

<400> SEQUENCE: 5
gttgctgggc acast                                                15

<210> SEQ ID NO 6
<211> LENGTH: 15
<212> TYPE: DNA
<213> ORGANISM: Artificial Sequence
<220> FEATURE:
<223> OTHER INFORMATION: ASO Forward Primer for Detecting Allele
      at PSs in Haplotypes Comprising Preferred Embodiments of Respons
      Markers I and Response Markers II
<220> FEATURE:
<221> NAME/KEY: misc_feature
<222> LOCATION: (14)..(14)
<223> OTHER INFORMATION: r is 'g' or 'a'

<400> SEQUENCE: 6
gaggggagag tccrt                                                15

<210> SEQ ID NO 7
<211> LENGTH: 15
<212> TYPE: DNA
<213> ORGANISM: Artificial Sequence
<220> FEATURE:
<223> OTHER INFORMATION: ASO Forward Primer for Detecting Allele
      at PSs in Haplotypes Comprising Preferred Embodiments of Respons
      Markers I and Response Markers II
<220> FEATURE:
<221> NAME/KEY: misc_feature
<222> LOCATION: (14)..(14)
<223> OTHER INFORMATION: k is 'g' or 't/u'

<400> SEQUENCE: 7
tgaagatgca gctkt                                                15

<210> SEQ ID NO 8
<211> LENGTH: 15
<212> TYPE: DNA
<213> ORGANISM: Artificial Sequence
<220> FEATURE:
<223> OTHER INFORMATION: ASO Reverse Primer for Detecting Allele
      at PSs in Haplotypes Comprising Preferred Embodiments of Respons
      Markers I and Response Markers II
<220> FEATURE:
<221> NAME/KEY: misc_feature
<222> LOCATION: (14)..(14)
<223> OTHER INFORMATION: s is 'g' or 'c'

<400> SEQUENCE: 8
cctgaacatg caast                                                15
```

```
<210> SEQ ID NO 9
<211> LENGTH: 15
<212> TYPE: DNA
<213> ORGANISM: Artificial Sequence
<220> FEATURE:
<223> OTHER INFORMATION: ASO Reverse Primer for Detecting Allele
      at PSs in Haplotypes Comprising Preferred Embodiments of Respons
      Markers I and Response Markers II
<220> FEATURE:
<221> NAME/KEY: misc_feature
<222> LOCATION: (14)..(14)
<223> OTHER INFORMATION: y is 't' or 'c'

<400> SEQUENCE: 9
gctcaaaact ccayg                                                    15

<210> SEQ ID NO 10
<211> LENGTH: 15
<212> TYPE: DNA
<213> ORGANISM: Artificial Sequence
<220> FEATURE:
<223> OTHER INFORMATION: ASO Reverse Primer for Detecting Allele
      at PSs in Haplotypes Comprising Preferred Embodiments of Respons
      Markers I and Response Markers II
<220> FEATURE:
<221> NAME/KEY: misc_feature
<222> LOCATION: (14)..(14)
<223> OTHER INFORMATION: m is 'a' or 'c'

<400> SEQUENCE: 10
tgggaaaggg ccama                                                    15

<210> SEQ ID NO 11
<211> LENGTH: 10
<212> TYPE: DNA
<213> ORGANISM: Artificial Sequence
<220> FEATURE:
<223> OTHER INFORMATION: Forward Primer Extension Oligo for Detecting
      Alleles at PSs in Haplotypes Comprising Preferred Embodiments of
      Response Markers I and Response Markers II

<400> SEQUENCE: 11
gctgggcaca                                                          10

<210> SEQ ID NO 12
<211> LENGTH: 10
<212> TYPE: DNA
<213> ORGANISM: Artificial Sequence
<220> FEATURE:
<223> OTHER INFORMATION: Forward Primer Extension Oligo for Detecting
      Alleles at PSs in Haplotypes Comprising Preferred Embodiments of
      Response Markers I and Response Markers II

<400> SEQUENCE: 12
gggagagtcc                                                          10

<210> SEQ ID NO 13
<211> LENGTH: 10
<212> TYPE: DNA
<213> ORGANISM: Artificial Sequence
<220> FEATURE:
<223> OTHER INFORMATION: Forward Primer Extension Oligo for Detecting
      Alleles at PSs in Haplotypes Comprising Preferred Embodiments of
      Response Markers I and Response Markers II

<400> SEQUENCE: 13
agatgcagct                                                          10
```

```
<210> SEQ ID NO 14
<211> LENGTH: 10
<212> TYPE: DNA
<213> ORGANISM: Artificial Sequence
<220> FEATURE:
<223> OTHER INFORMATION: Reverse Primer Extension Oligo for Detecting
      Alleles at PSs in Haplotypes Comprising Preferred Embodiments of
      Response Markers I and Response Markers II

<400> SEQUENCE: 14
gaacatgcaa                                                           10

<210> SEQ ID NO 15
<211> LENGTH: 10
<212> TYPE: DNA
<213> ORGANISM: Artificial Sequence
<220> FEATURE:
<223> OTHER INFORMATION: Reverse Primer Extension Oligo for Detecting
      Alleles at PSs in Haplotypes Comprising Preferred Embodiments of
      Response Markers I and Response Markers II

<400> SEQUENCE: 15
caaaactcca                                                           10

<210> SEQ ID NO 16
<211> LENGTH: 10
<212> TYPE: DNA
<213> ORGANISM: Artificial Sequence
<220> FEATURE:
<223> OTHER INFORMATION: Reverse Primer Extension Oligo for Detecting
      Alleles at PSs in Haplotypes Comprising Preferred Embodiments of
      Response Markers I and Response Markers II

<400> SEQUENCE: 16
gaaagggcca                                                           10

<210> SEQ ID NO 17
<211> LENGTH: 10
<212> TYPE: DNA
<213> ORGANISM: Artificial Sequence
<220> FEATURE:
<223> OTHER INFORMATION: 10 base universal tag

<400> SEQUENCE: 17
agcggataac                                                           10

<210> SEQ ID NO 18
<211> LENGTH: 29
<212> TYPE: DNA
<213> ORGANISM: Artificial Sequence
<220> FEATURE:
<223> OTHER INFORMATION: Forward PCR CDK5-specific Primer Sequence used
      in hME Assays

<400> SEQUENCE: 18
agcggataac ttctaccgcg gaggcaaac                                      29

<210> SEQ ID NO 19
<211> LENGTH: 30
<212> TYPE: DNA
<213> ORGANISM: Artificial Sequence
<220> FEATURE:
<223> OTHER INFORMATION: Forward PCR CDK5-specific Primer Sequence used
      in hME Assays

<400> SEQUENCE: 19
agcggataac aatgactggg aggagagagg                                     30
```

```
<210> SEQ ID NO 20
<211> LENGTH: 30
<212> TYPE: DNA
<213> ORGANISM: Artificial Sequence
<220> FEATURE:
<223> OTHER INFORMATION: Forward PCR CDK5-specific Primer Sequence used
      in hME Assays

<400> SEQUENCE: 20
agcggataac atcactgccc tcacccattg                                   30

<210> SEQ ID NO 21
<211> LENGTH: 30
<212> TYPE: DNA
<213> ORGANISM: Artificial Sequence
<220> FEATURE:
<223> OTHER INFORMATION: Forward PCR CDK5-specific Primer Sequence used
      in hME Assays

<400> SEQUENCE: 21
agcggataac ctcaccctgc ccctgaagat                                   30

<210> SEQ ID NO 22
<211> LENGTH: 30
<212> TYPE: DNA
<213> ORGANISM: Artificial Sequence
<220> FEATURE:
<223> OTHER INFORMATION: Reverse PCR CDK5-specific Primer Sequence used
      in hME Assays

<400> SEQUENCE: 22
agcggataac aaacggacac gcgttgcttc                                   30

<210> SEQ ID NO 23
<211> LENGTH: 30
<212> TYPE: DNA
<213> ORGANISM: Artificial Sequence
<220> FEATURE:
<223> OTHER INFORMATION: Reverse PCR CDK5-specific Primer Sequence used
      in hME Assays

<400> SEQUENCE: 23
agcggataac aaccaggtgc tgaaaggtgg                                   30

<210> SEQ ID NO 24
<211> LENGTH: 30
<212> TYPE: DNA
<213> ORGANISM: Artificial Sequence
<220> FEATURE:
<223> OTHER INFORMATION: Reverse PCR CDK5-specific Primer Sequence used
      in hME Assays

<400> SEQUENCE: 24
agcggataac tatccttgct ttcctctgcc                                   30

<210> SEQ ID NO 25
<211> LENGTH: 30
<212> TYPE: DNA
<213> ORGANISM: Artificial Sequence
<220> FEATURE:
<223> OTHER INFORMATION: Reverse PCR CDK5-specific Primer Sequence used
      in hME Assays

<400> SEQUENCE: 25
agcggataac ggagtcaagg atcacttggg                                   30
```

```
<210> SEQ ID NO 26
<211> LENGTH: 22
<212> TYPE: DNA
<213> ORGANISM: Artificial Sequence
<220> FEATURE:
<223> OTHER INFORMATION: Extension Primer for Genotyping CDK5
      Polymorphic Sites

<400> SEQUENCE: 26
ggaggcaaac cttggacttc aa                                              22

<210> SEQ ID NO 27
<211> LENGTH: 21
<212> TYPE: DNA
<213> ORGANISM: Artificial Sequence
<220> FEATURE:
<223> OTHER INFORMATION: Extension Primer for Genotyping CDK5
      Polymorphic Sites

<400> SEQUENCE: 27
tcagacgccc tgaacatgca a                                               21

<210> SEQ ID NO 28
<211> LENGTH: 24
<212> TYPE: DNA
<213> ORGANISM: Artificial Sequence
<220> FEATURE:
<223> OTHER INFORMATION: Extension Primer for Genotyping CDK5
      Polymorphic Sites

<400> SEQUENCE: 28
tcacccattg tgctcaaaac tcca                                            24

<210> SEQ ID NO 29
<211> LENGTH: 17
<212> TYPE: DNA
<213> ORGANISM: Artificial Sequence
<220> FEATURE:
<223> OTHER INFORMATION: Extension Primer for Genotyping CDK5
      Polymorphic Sites

<400> SEQUENCE: 29
cccctgaaga tgcagct                                                    17
```

CDK5 GENETIC MARKERS ASSOCIATED WITH GALANTAMINE RESPONSE

This application claims benefit of application Ser. No. 60/530,000 filed Dec. 15, 2003.

FIELD OF THE INVENTION

This invention relates to the field of genomics and pharmacogenetics. More specifically, this invention relates to variants of the gene for cyclin-dependent kinase-5 (CDK5) and their use as predictors of an individual's response to galantamine.

BACKGROUND OF THE INVENTION

Alzheimer's disease (AD) is a fatal degenerative disorder of the central nervous system that affects an estimated 3%-4% of the United States population above the age of 65 (Katzman, *Arch. Neurol.* 33:217-8 (1976)). AD is characterized by profound memory impairment, emotional disturbance, and in late stages, personality changes (Bartolucci et al., *Proteins* 42:182-91 (2001)). Molecular symptoms include neuronal loss, synaptic damage, and increased levels of neurofibrillary tangles, neuritic plaques, and granulovacuolar degeneration. The reduced cognitive function seen in patients with AD are thought to be primarily related to the degeneration of cholinergic neurons in the cortex and hippocampus, which results in deficits of cholinergic transmission and reduced levels of acetylcholine (Scott et al., *Drugs* 60 (5):1095-1122 (2000)). Studies have shown that AD is associated with decreased levels of choline acetyltransferase (CHAT) and nicotinic acetylcholine receptors (nAChRs) (Bartolucci et al., supra).

Since there is no cure for AD at the present time, current treatment for AD patients focuses on relieving some of the symptoms associated with this disease. The major strategies revolve around increasing central cholinergic function by elevating the transient levels of acetylcholine in the brain (cholinergic therapy). Current drugs for elevating acetylcholine levels are AChE inhibitors, which decrease the degradation of acetylcholine in the synaptic cleft, allowing for increased neuronal transmission, and nicotinic agonists, which directly enhance the function of nAChRs (Scott et al., supra; Bartolucci et al., supra).

Cholinergic therapy may also have beneficial effects for mild or minimal cognitive impairment (MCI). MCI is a condition characterized by subtle cognitive deficits not severe enough to be classified as true dementia, but in many patients represents an early stage of AD (Almkvist et al., *J. Neural Transm. Suppl.* 54: 21-29 (1998)). Thus, if drug therapy to enhance cognition is started when the symptoms of dementia first appear, even before a clinical diagnosis of AD, it is possible that the onset of AD may be delayed (Small, *Hippocrates* 14(9) (2000)). Other cognitive disorders that may benefit from cholinergic therapy are vascular dementias and Lewy body dementias.

One compound that has been approved in the United States for the treatment of mild to moderate dementia of the Alzheimer's type is galantamine, which is a tertiary alkaloid, and marketed as Reminyl® (galantamine hydrobromide) by Janssen Pharmaceuticals (Scott et al., *Drugs* 60(5):1095-1122 (2000)). Although clinical trials have established galantamine's efficacy in producing significant improvement in cognitive function and activities of daily living in AD patients as compared to placebo treatment (Raskind et al., *Neurology* 54:2261-8 (2000); Coyle et al., *Biol. Psychiatry* 49:289-99 (2001); Rockwood et al., *J. Neurol. Nerurosurg. Psychiatry* 71:589-595 (2001)), it is not clear whether or not all patients with mild to moderate AD will ultimately demonstrate a clinically meaningful improvement in cognitive function, suggesting that there may be variability in an individual's response to pharmaceutical agents to treat cognitive impairment. However, physicians currently are unable to identify patients who are at risk for reduced or lack of efficacy of galantamine therapy, which can be expensive and is not without risk of side effects, with the most common side effects being nausea, vomiting, diarrhea, dizziness and anorexia (Wilcock et al., *BMJ* 321:1-7 (2000); Scott et al., supra). Thus it would be useful to understand the biological basis for the variability of response to galantamine.

Variability in the efficacy and toxicity of a number of drugs has been correlated with genetic variation in proteins involved in drug metabolism (Evans et al., *Science* 286:487-91 (1999)). Metabolism of galantamine is primarily mediated by the cytochrome p-450 enzyme system, specifically the isozymes 2D6 and 3A4 (CYP2D6 and CYP3A4) (Scott et al., supra). Poor CYP2D6 metabolizers exhibit about 25% less clearance of galantamine than extensive CYP2D6 metabolizers, although this difference is not considered to be clinically relevant because the recommended dosage regimen is to individually titrate the dose to tolerability (Reminyl® tablets prescribing information, Janssen Pharmaceutica Products, March 2001). In addition, while several metabolites of galantamine inhibit AChE in vitro, their in vivo activity is not considered to be clinically relevant (Scott et al., supra).

Another potential source of variability of response to galantamine could be genetic variation in proteins involved in the etiology of AD or its severity, or in the mechanism of action of galantamine. For example, as many as 70% of AD patients have a particular single nucleotide polymorphism in the gene encoding apolipoprotein E (the ApoE4 allele) that appears to be correlated with a greater impairment of cholinergic function and a study with the ACHE inhibitor tacrine suggested that the presence of this polymorphism is correlated with reduced response to treatment (Farlow et al., *Neurology* 50:669-77 (1998)). However, other studies with galantamine showed no significant difference in efficacy of response between patients with zero, one or two copies of the ApoE4 allele (Raskind et al., supra; Aerssens et al., poster presented at 7$^{th}$ International World Alzheimer's Congress, Jul. 9-18, 2000, Washington, D.C.).

One protein whose deregulation may be involved in neurodegenerative disease is CDK5, a serine/threonine kinase (Zheng et al., *Eur. J. Biochem.* 269(18):4427-34 (2002)), which is encoded by a gene on chromosome 7q36 that consists of 12 exons. Required for normal mammalian central nervous system development, CDK5 is activated by its neuron-specific activator, p35, and phosphorylates both high molecular weight neurofilaments and microtubule-associated protein tau (Hashiguchi et al., *J. Biol. Chem.* 277(46):4425-30 (2002)). p25, a calpain digested tuncated form of p35, has been found to accumulate in the neurons of Alzheimer's patients (Tseng et al., *FEBS Lett.* 523(1-3):58-62 (2002)). Unlike p35, p25 is not readily degraded, and the binding of p25 to CDK5 constitutively activates CDK5, changes its cellular location, alters its substrate specificity, and increases its phosphorylation of serine(202)/theonine (205) in tau (Hashiguchi et al., supra). This hyperphosphorylation reduces the ability of tau to associate with microtubules leading to cytoskeletal disruption, morphologic degeneration, and apoptosis (Patrick et al., *Nature* 402 (6762):615-22 (1999); Liu et al., *FEBS Lett.* 530(1-3):209-14 (2002)).

Recently, various haplotypes of the CHRNA2, EPHX2, and LRPAP1 genes—three genes either directly or indirectly involved in the etiology of cognitive disorders, namely AD in the case of CHRNA2 and LRPAP1, and Parkinson's Disease in the case of EPHX2—were discovered to exist in a cohort of Alzheimer's patients, and were discovered to be associated with a response to galantamine therapy. Because of its involvement in the etiology of AD, CDK5 is a logical candidate for a determination of whether CDK5 haplotypes are similarly associated with response to galantamine therapy.

SUMMARY OF THE INVENTION

Accordingly, the inventors herein have discovered a set of haplotypes in the CDK5 gene that are associated with response to galantamine. The inventors have also discovered that the copy number of each of these CDK5 haplotypes affects the level of galantamine response. The CDK5 haplotypes are shown in Table 1 below.

TABLE 1

CDK5 Haplotypes Having Association with Response to Galantamine[1]

| Haplotype | Polymorphic Site (PS) | | | |
|---|---|---|---|---|
| | 1 | 2 | 3 | 4 |
| (1) | | | G | G |
| (2) | | G | G | G |

[1]The absence of a PS entry for a haplotype indicates that the PS is not part of the marker.

If an individual has zero copies of any of haplotypes (1)-(2) in Table 1, then that individual is defined as having a "response marker I" and is more likely to respond to galantamine than an individual having one copy of any of haplotypes (1)-(2) in Table 1, such individual being defined as having a "response marker II," or two copies of any of haplotypes (1)-(2) in Table 1, such individual being defined as having a "response marker III." Also, an individual having a response marker II is more likely to respond to galantamine than an individual having a response marker III. Information about the composition of each of haplotypes (1)-(2), namely the location in the CDK5 gene of each of the polymorphic sites (PSs), and the identity of the reference and variant allele at each PS, can be found in Table 2, shown below.

TABLE 2

Polymorphic Sites Identified in the CDK5 Gene of Caucasian Individuals with Alzheimer's Disease

| PS Number | Poly ID[1] | Location | Position in FIG. 1/SEQ ID NO: 1 | Reference Allele | Variant Allele |
|---|---|---|---|---|---|
| 1 | 44504282 | promoter | 1670 | C | G |
| 2 | 44510007 | intron 5 | 3892 | G | C |
| 3 | 44510316 | intron 9 | 4808 | A | G |
| 4 | 44511200 | intron 9 | 5284 | G | T |

[1]The Poly ID is a unique identifier assigned to the indicated PS by Genaissance Pharmaceuticals, Inc., New Haven, CT.

In addition, as described in more detail below, the inventors believe that additional haplotypes may readily be identified based on linkage disequilibrium between any of the above CDK5 haplotypes and another haplotype located in the CDK5 gene or another gene, or between an allele at one or more of the PSs in the above haplotypes and an allele at another PS located in the CDK5 gene or another gene. In particular, such haplotypes include haplotypes that are in linkage disequilibrium with any of haplotypes (1)-(2) in Table 1, hereinafter referred to as "linked haplotypes," as well as "substitute haplotypes" for any of haplotypes (1)-(2) in which one or more of the polymorphic sites (PSs) in the original haplotype is substituted with another PS, wherein the allele at the substituted PS is in linkage disequilibrium with the allele at the substituting PS.

In one aspect, the invention provides methods and kits for determining whether an individual has a response marker I, a response marker II, or a response marker III. These methods and kits are useful for predicting the expected therapeutic response of an individual to treatment with galantamine.

In one embodiment, a method is provided for determining whether an individual has a response marker I, a response marker II, or a response marker III comprising determining whether the individual has zero, one, or two copies of any of (a) haplotypes (1)-(2) in Table 1, (b) a linked haplotype for any of haplotypes (1)-(2) in Table 1, and (c) a substitute haplotype for any of haplotypes (1)-(2) in Table 1.

In another embodiment of the invention, a method is provided for assigning an individual to a first, second, or third response marker group comprising determining whether the individual has zero, one, or two copies of any of (a) haplotypes (1)-(2) in Table 1, (b) a linked haplotype for any of haplotypes (1)-(2) in Table 1, and (c) a substitute haplotype for any of haplotypes (1)-(2) in Table 1, and assigning the individual to a response marker group based on the copy number of that haplotype. The individual is assigned to the first response marker group if the individual has zero copies of any of (a) haplotypes (1)-(2) in Table 1, (b) a linked haplotype for any of haplotypes (1)-(2) in Table 1, and (c) a substitute haplotype for any of haplotypes (1)-(2) in Table 1, to the second response marker group if the individual has one copy of any of (a) haplotypes (1)-(2) in Table 1, (b) a linked haplotype for any of haplotypes (1)-(2) in Table 1, and (c) a substitute haplotype for any of haplotypes (1)-(2) in Table 1, and to the third response marker group if the individual has two copies of any of (a) haplotypes (1)-(2) in Table 1, (b) a linked haplotype for any of haplotypes (1)-(2) in Table 1, and (c) a substitute haplotype for any of haplotypes (1)-(2) in Table 1.

One embodiment of a kit for determining whether an individual has a response marker I, a response marker II, or a response marker III comprises a set of oligonucleotides designed for identifying at least one of the alleles present at each PS in a set of one or more PSs. The set of one or more PSs comprises the set of one or more PSs for any of the haplotypes in Table 1, the set of one or more PSs for a linked haplotype, or the set of one or more PSs for a substitute haplotype. In a further embodiment, the kit comprises a manual with instructions for performing one or more reactions on a human nucleic acid sample to identify the allele(s) present in the individual at each PS in the set and determining if the individual has a response marker I, a response marker II, or a response marker III based on the identified allele(s).

In yet another embodiment, the invention provides a method for predicting an individual's response to treatment with galantamine. The method comprises determining whether the individual has a response marker I, a response marker II, or a response marker III, and making a response prediction based on the results of the determining step. If the individual is determined to have a response marker I, then the response prediction is that the individual is more likely to respond to galantamine treatment than an individual having a response marker II or a response marker III. If the individual is determined to have a response marker II, then the response prediction is that the individual is less likely to respond to galantamine treatment than an individual having a response marker I, and more likely to respond to galantamine treatment than an individual having a response marker III. If the individual is determined to have a response marker III, then the response prediction is that the individual is less likely to respond to galantamine treatment than an individual having a response marker I or a response marker II.

In other aspects, the invention provides (i) a method for seeking regulatory approval for marketing a galantamine pharmaceutical formulation to a population having a cognitive disorder, wherein the population is partially or wholly defined by having a response marker I or a response marker II, (ii) an article of manufacture comprising the pharmaceutical formulation, (iii) a method for manufacturing a drug product comprising the pharmaceutical formulation, and (iv) a method for marketing the drug product. In a preferred embodiment, the cognitive disorder is mild to moderate dementia of the Alzheimer's type, dementia associated with Parkinson's Disease, MCI, a vascular dementia or a Lewy body dementia.

The method for seeking regulatory approval comprises conducting at least one clinical trial which comprises administering the pharmaceutical formulation and a placebo to each of a first, second, third, and fourth treatment group of individuals having a cognitive disorder, wherein each individual in the first treatment group has a response marker I, each individual in the second treatment group does not have a response marker I, each individual in the third treatment group has a response marker II, and each individual in the fourth treatment group has a response marker III, demonstrating that the first treatment group is more likely to respond to the pharmaceutical formulation than the second treatment group, demonstrating that the third treatment group is more likely to respond to the pharmaceutical formulation than the fourth treatment group, and filing with a regulatory agency an application for marketing approval of the pharmaceutical formulation with a label stating that the pharmaceutical formulation is indicated for a population having a cognitive disorder, and further stating that individuals having a response marker I are more likely to respond to the pharmaceutical formulation than individuals having a response marker II or a response marker III, and that individuals having a response marker II are more likely to respond to the pharmaceutical formulation than individuals having a response marker III. In preferred embodiments, the regulatory agency is the United States Food and Drug Administration (FDA) or the European Agency for the Evaluation of Medicinal Products (EMEA), or a future equivalent of these agencies.

In one embodiment, the article of manufacture comprises the pharmaceutical formulation and at least one indicium identifying a population for whom the pharmaceutical formulation is indicated, wherein the identified population is one having a cognitive disorder, and wherein the identified population is partially or wholly defined by having a response marker I or a response marker II, wherein a trial population of individuals having a response marker I is more likely to respond to the formulation than a trial population lacking a response marker I, and a trial population of individuals having a response marker II is more likely to respond to the formulation than a trial population of individuals lacking both a response marker I and a response marker II. Another embodiment of the article of manufacture comprises packaging material and the pharmaceutical formulation contained within the packaging material, wherein the packaging material comprises a label approved by a regulatory agency for the pharmaceutical formulation, wherein the label states that the pharmaceutical formulation is indicated for improving cognitive function in a population having a cognitive disorder, wherein the population is partially or wholly defined by having a response marker I or a response marker II, and further stating that those members of the population having a response marker I are more likely to respond to the pharmaceutical formulation than those members lacking a response marker I, and those members of the population having a response marker II are more likely to respond to the pharmaceutical formulation than those members lacking both a response marker I and a response marker II. Preferably, the pharmaceutical formulation comprises a galantamine compound as at least one active ingredient. The galantamine compound is selected from galantamine, a galantamine derivative, and pharmaceutically acceptable salts of galantamine or the galantamine derivative.

The method for manufacturing the drug product comprises combining in a package a pharmaceutical formulation comprising a galantamine compound as at least one active ingredient and a label which states that the drug product is indicated for a population having a cognitive disorder, wherein the population is partially or wholly defined by having a response marker I or a response marker II, wherein those members of the population having a response marker I are more likely to respond to the drug product than those members of the population lacking a response marker I, and those members of the population having a response marker II are more likely to respond to the drug product than those members of the population lacking both a response marker I and a response marker II. The galantamine compound is selected from galantamine, a galantamine derivative, and pharmaceutically acceptable salts of galantamine or the galantamine derivative.

The method for marketing the drug product comprises promoting to a target audience the use of the drug product for treating individuals who belong to the defined population.

BRIEF DESCRIPTION OF THE FIGURES

FIG. 1A-C illustrates a reference sequence for the CDK5 gene (contiguous lines; SEQ ID NO:1), with the start and stop positions of each region of coding sequence indicated with a bracket ([or]) and the numerical position below the sequence and the polymorphic site(s) and polymorphism(s) identified by Applicants in the patient cohort indicated by the variant nucleotide positioned below the polymorphic site in the sequence.

DEFINITIONS

In the context of this disclosure, the terms below shall be defined as follows unless otherwise indicated:

Allele—A particular form of a genetic locus, distinguished from other forms by its particular nucleotide sequence, or one of the alternative polymorphisms found at a polymorphic site.

Gene—A segment of DNA that contains the coding sequence for a protein, wherein the segment may include promoters, exons, introns, and other untranslated regions that control expression.

Genotype—An unphased 5' to 3' sequence of nucleotide pair(s) found at a set of one or more polymorphic sites in a locus on a pair of homologous chromosomes in an individual. As used herein, genotype includes a full-genotype and/or a sub-genotype as described below.

Genotyping—A process for determining a genotype of an individual.

Haplotype—A 5' to 3' sequence of nucleotides found at a set of one or more polymorphic sites in a locus on a single chromosome from a single individual.

Haplotype pair—The two haplotypes found for a locus in a single individual.

Haplotyping—A process for determining one or more haplotypes in an individual and includes use of family pedigrees, molecular techniques and/or statistical inference.

Haplotype data—Information concerning one or more of the following for a specific gene: a listing of the haplotype pairs in an individual or in each individual in a population; a listing of the different haplotypes in a population; frequency of each haplotype in that or other populations, and any known associations between one or more haplotypes and a trait.

Isolated—As applied to a biological molecule such as RNA, DNA, oligonucleotide, or protein, isolated means the molecule is substantially free of other biological molecules such as nucleic acids, proteins, lipids, carbohydrates, or other material such as cellular debris and growth media. Generally, the term "isolated" is not intended to refer to a complete absence of such material or to absence of water, buffers, or salts, unless they are present in amounts that substantially interfere with the methods of the present invention.

Locus—A location on a chromosome or DNA molecule corresponding to a gene or a physical or phenotypic feature, where physical features include polymorphic sites.

Nucleotide pair—The nucleotides found at a polymorphic site on the two copies of a chromosome from an individual.

Phased—As applied to a sequence of nucleotide pairs for two or more polymorphic sites in a locus, phased means the combination of nucleotides present at those polymorphic sites on a single copy of the locus is known.

Polymorphic site (PS)—A position on a chromosome or DNA molecule at which at least two alternative sequences are found in a population.

Polymorphism—The sequence variation observed in an individual at a polymorphic site. Polymorphisms include nucleotide substitutions, insertions, deletions and microsatellites and may, but need not, result in detectable differences in gene expression or protein function.

Polynucleotide—A nucleic acid molecule comprised of single-stranded RNA or DNA or comprised of complementary, double-stranded DNA.

Population Group—A group of individuals sharing a common ethnogeographic origin.

Reference Population—A group of subjects or individuals who are predicted to be representative of the genetic variation found in the general population. Typically, the reference population represents the genetic variation in the population at a certainty level of at least 85%, preferably at least 90%, more preferably at least 95% and even more preferably at least 99%.

Single Nucleotide Polymorphism (SNP)—Typically, the specific pair of nucleotides observed at a single polymorphic site. In rare cases, three or four nucleotides may be found.

Subject—A human individual whose genotypes or haplotypes or response to treatment or disease state are to be determined.

Treatment—A stimulus administered internally or externally to a subject.

Unphased—As applied to a sequence of nucleotide pairs for two or more polymorphic sites in a locus, unphased means the combination of nucleotides present at those polymorphic sites on a single copy of the locus is not known.

DESCRIPTION OF THE PREFERRED EMBODIMENTS

Each response marker of the invention is a combination of a particular haplotype and the copy number for that haplotype. Preferably, the haplotype is one of the haplotypes shown in Table 1. The PS or PSs in these haplotypes are referred to herein as PS1, PS2, PS3, and PS4, and are located in the CDK5 gene at positions corresponding to those identified in FIG. 1/SEQ ID NO:1 (see Table 2 for summary of PS1, PS2, PS3, and PS4, and locations). In describing the PSs in the response markers of the invention, reference is made to the sense strand of a gene for convenience. However, as recognized by the skilled artisan, nucleic acid molecules containing a particular gene may be complementary double stranded molecules and thus reference to a particular site or haplotype on the sense strand refers as well to the corresponding site or haplotype on the complementary antisense strand. Further, reference may be made to detecting a genetic marker or haplotype for one strand and it will be understood by the skilled artisan that this includes detection of the complementary haplotype on the other strand.

As described in more detail in the examples below, the response markers of the invention are based on the discovery by the inventors of associations between certain haplotypes in the CDK5 gene and response to galantamine treatment in a cohort of individuals diagnosed with Alzheimer's Disease.

In particular, the inventors herein discovered that a haplotype comprising guanine at PS3 and guanine at PS4 (haplotype (1) in Table 1) affected the response to galantamine of the patients participating in the study. The group of patients having zero copies of this haplotype experienced a better response to galantamine than the patient group having one copy, which experienced a better response to galantamine than the patient group having two copies. As used herein, the terms "galantamine response" and "response to galantamine," are intended to refer to the change in an individual's cognitive function, preferably as measured by his/her score on the cognitive subscale of the Alzheimer's Disease Assessment (ADAS-cog) (Rosen et al., *Am. J. Psychiatry* 141:1356-64 (1984); Rockwood et al., *J. Neurol. Neurosurg. Psychiatry* 71:589-95 (2001); Tariot et al., *Neurology* 54:2269-76 (2000); Wilcock et al., *BMJ* 321:1-7 (2000)) following galantamine treatment/administration. The ADAS-cog measures cognitive function, including spoken language ability, comprehension of spoken language, recall of test instructions, word-finding difficulty in spontaneous speech, following commands, naming objects and fingers, constructional praxis, ideational praxis, orientation, word-recall task and word-recognition task (*Alzhe-* imer's Insights Online, Vol. 3, No. 1, 1997). With regard to the ADAS-cog, the lower the score, the better the cognitive function. Thus, a downward change in the ADAS-cog following galantamine treatment/administration indicates a "good" or "positive" or "better" response to galantamine (or, simply, "response"), and an upward change, or no change, in the ADAS-cog following galantamine treatment/administration indicates a "bad" or "negative" or "worse" response to galantamine (or, simply, "non-reponse"). Additionally, an individual's response to galantamine may be measured by other scientifically accepted rating scales for cognitive function, including, but not limited to, Behavioral Pathology in Alzheimer's Disease Rating Scale (BEHAVE-AD), Blessed Test, CANTAB (CAmbridge Neuropsychological Test Automated Battery), CERAD (The Consortium to Establish a Registry for Alzheimer's Disease) Clinical and Neuropsychological Tests, Clock Draw Test, Cornell Scale for Depression in Dementia (CSDD), Geriatric Depression Scale (GDS), Mini Mental State Exam (MMSE), Neuropsychiatric Inventory (NPI), and The 7 Minute Screen.

Moreover, as shown in Tables 10A, 10B, and 10C below, the different effect of copy number of haplotype (1) on galantamine response is statistically significant. Therefore, this haplotype, in combination with the haplotype copy number, can be used to differentiate the galantamine response that might be observed in an individual or a trial population after treatment with galantamine. Consequently, zero copies of haplotype (1) in Table 1 is referred to herein as a response marker I, one copy of haplotype (1) in Table 1 is referred to herein as a response marker II, and two copies of haplotype (1) in Table 1 is referred to herein as a response marker III.

In addition, the skilled artisan would expect that there might be additional PSs in the CDK5 gene or elsewhere on chromosome 7, wherein an allele at that PS is in high linkage disequilibrium (LD) with an allele at one or more of the PSs in the haplotypes comprising a response marker I, a response marker II, or a response marker III. Two particular alleles at different PSs are said to be in LD if the presence of the allele at one of the sites tends to predict the presence of the allele at the other site on the same chromosome (Stevens, *Mol. Diag.* 4:309-17 (1999)). One of the most frequently used measures of linkage disequilibrium is $\Delta^2$, which is calculated using the formula described by Devlin et al. (*Genomics* 29 (2):311-22 (1995)). $\Delta^2$ is the measure of how well an allele X at a first PS predicts the occurrence of an allele Y at a second PS on the same chromosome. The measure only reaches 1.0 when the prediction is perfect (e.g., X if and only if Y).

Thus, the skilled artisan would expect that all of the embodiments of the invention described herein may frequently be practiced by substituting any (or all) of the specifically identified CDK5 PSs in a response marker with another PS, wherein an allele at the substituted PS is in LD with an allele at the "substituting" PS. This "substituting" PS may be one that is currently known or subsequently discovered and may be present in the CDK5 gene, in a genomic region of about 100 kilobases spanning the CDK5 gene, or elsewhere on chromosome 7.

Further, the inventors contemplate that there will be other haplotypes in the CDK5 gene or elsewhere on chromosome 7 that are in LD with one or more of the haplotypes in Table 1 that would therefore also be predictive of galantamine response. Preferably, the linked haplotype is present in the CDK5 gene or in a genomic region of about 100 kilobases spanning the CDK5 gene. The linkage disequilibrium between the haplotypes in Table 1 and such linked haplotypes can also be measured using $\Delta^2$.

In preferred embodiments, the linkage disequilibrium between an allele at a polymorphic site in any of the haplotypes in Table 1 and an allele at a "substituting" polymorphic site, or between any of the haplotypes in Table 1 and a linked haplotype, has a $\Delta^2$ value, as measured in a suitable reference population, of at least 0.75, more preferably at least 0.80, even more preferably at least 0.85 or at least 0.90, yet more preferably at least 0.95, and most preferably 1.0. A suitable reference population for this $\Delta^2$ measurement is preferably a population for which the distribution of its members reflects that of the population of patients to be treated with galantamine. The reference population may be the general population, a population using galantamine, a population with AD or AD risk factors, or the like.

LD patterns in genomic regions are readily determined empirically in appropriately chosen samples using various techniques known in the art for determining whether any two alleles (either those occurring at two different PSs or two haplotypes for two different multi-site loci) are in linkage disequilibrium (GENETIC DATA ANALYSIS II, Weir, Sinauer Associates, Inc. Publishers, Sunderland, Mass., 1996). The skilled artisan may readily select which method of determining LD will be best suited for a particular sample size and genomic region.

As described above and in the examples below, the response markers of the invention are associated with changes in the cognitive subscale of the Alzheimer's Disease Assessment Scale (ADAS-cog) in response to galantamine treatment. Thus, the invention provides a method and kit for determining whether an individual has a response marker I, a response marker II, or a response marker III. A response marker I is zero copies of any of (a) haplotypes (1)-(2) in Table 1, (b) a linked haplotype for any of haplotypes (1)-(2) in Table 1, and (c) a substitute haplotype for any of haplotypes (1)-(2) in Table 1. A response marker II is one copy of any of (a) haplotypes (1)-(2) in Table 1, (b) a linked haplotype for any of haplotypes (1)-(2) in Table 1, and (c) a substitute haplotype for any of haplotypes (1)-(2) in Table 1. A response marker III is two copies of any of (a) haplotypes (1)-(2) in Table 1, (b) a linked haplotype for any of haplotypes (1)-(2) in Table 1, and (c) a substitute haplotype for any of haplotypes (1)-(2) in Table 1.

In one embodiment, the invention provides a method for determining whether an individual has a response marker I, a response marker II, or a response marker III. The method comprises determining whether the individual has zero copies, one copy, or two copies of any of (a) haplotypes (1)-(2) in Table 1, (b) a linked haplotype for any of haplotypes (1)-(2) in Table 1, and (c) a substitute haplotype for any of haplotypes (1)-(2) in Table 1.

In some embodiments, the individual is Caucasian and may be diagnosed with a cognitive disorder, such as mild to moderate dementia of the Alzheimer's type, dementia associated with Parkinson's Disease, MCI, a vascular dementia, and Lewy body dementia, may have risk factors associated with a cognitive disorder, or may be a candidate for treatment with galantamine for an alternative reason.

In another embodiment, the invention provides a method for assigning an individual to a first, second, or third response marker group. The method comprises determining whether the individual has zero copies, one copy, or two copies of any of (a) haplotypes (1)-(2) in Table 1, (b) a linked haplotype for any of haplotypes (1)-(2) in Table 1, and (c) a substitute haplotype for any of haplotypes (1)-(2) in Table 1, and assigning the individual to the first response marker group if the individual has zero copies of any of (a) haplotypes (1)-(2) in Table 1, (b) a linked haplotype for any of haplotypes (1)-(2) in Table 1, assigning the individual to the second response marker group if the individual has one copy of any of (a) haplotypes (1)-(2) in Table 1, (b) a linked haplotype for any of haplotypes (1)-(2) in Table 1, and (c) a substitute haplotype for any of haplotypes (1)-(2) in Table 1, and assigning the individual to the third response marker group if the individual has two copies of any of (a) haplotypes (1)-(2) in Table 1, (b) a linked haplotype for any of haplotypes (1)-(2) in Table 1, and (c) a substitute haplotype for any of haplotypes (1)-(2) in Table 1.

In some embodiments, the individual is Caucasian and may be diagnosed with a cognitive disorder, such as mild to moderate dementia of the Alzheimer's type, dementia associated with Parkinson's Disease, MCI, a vascular dementia, and Lewy body dementia, may have risk factors associated with a cognitive disorder, or may be a candidate for treatment with galantamine for an alternative reason.

The presence in an individual of a response marker I, a response marker II, or a response marker III may be determined by a variety of indirect or direct methods well known in the art for determining haplotypes or haplotype pairs for a set of one or more PSs in one or both copies of the individual's genome, including those discussed below. The genotype for a PS in an individual may be determined by methods known in the art or as described below.

One indirect method for determining whether zero copies, one copy, or two copies of a haplotype is present in an individual is by prediction based on the individual's genotype determined at one or more of the PSs comprising the haplotype and using the determined genotype at each site to determine the haplotypes present in the individual. The presence of zero copies, one copy, or two copies of a haplotype of interest can be determined by visual inspection of the alleles at the PS that comprise the haplotype. The haplotype pair is assigned by comparing the individual's genotype with the genotypes at the same set of PS corresponding to the haplotype pairs known to exist in the general population or in a specific population group or to the haplotype pairs that are theoretically possible based on the alternative alleles possible at each PS, and determining which haplotype pair is most likely to exist in the individual.

In a related indirect haplotyping method, the presence in an individual of zero copies, one copy, or two copies of a haplotype is predicted from the individual's genotype for a set of PSs comprising the selected haplotype using information on haplotype pairs known to exist in a reference population. In one embodiment, this haplotype pair prediction method comprises identifying a genotype for the individual at the set of PSs comprising the selected haplotype, accessing data containing haplotype pairs identified in a reference population for a set of PSs comprising the PSs of the selected haplotype, and assigning to the individual a haplotype pair that is consistent with the individual's genotype. Whether the individual has a response marker I, a response marker II, or a response marker III can be subsequently determined based on the assigned haplotype pair. The haplotype pair can be assigned by comparing the individual's genotype with the genotypes corresponding to the haplotype pairs known to exist in the general population or in a specific population group, and determining which haplotype pair is consistent with the genotype of the individual. In some embodiments, the comparing step may be performed by visual inspection. When the genotype of the individual is consistent with more than one haplotype pair, frequency data may be used to determine which of these haplotype pairs is most likely to be present in the individual. If a particular haplotype pair consistent with the genotype of the individual is more frequent in the reference population than other pairs consistent with the genotype, then that haplotype pair with the highest frequency is the most likely to be present in the individual. The haplotype pair frequency data used in this determination is preferably for a reference population coimprising the same ethnogeographic group as the individual. This determination may also be performed in some embodiments by visual inspection. In other embodiments, the comparison may be made by a computer-implemented algorithm with the genotype of the individual and the reference haplotype data stored in computer-readable formats. For example, as described in WO 01/80156, one computer-implemented algorithm to perform this comparison entails enumerating all possible haplotype pairs which are consistent with the genotype, accessing data containing haplotype pairs frequency data determined in a reference population to determine a probability that the individual has a possible haplotype pair, and analyzing the determined probabilities to assign a haplotype pair to the individual.

Typically, the reference population is composed of randomly selected individuals representing the major ethnogeographic groups of the world. A preferred reference population for use in the methods of the present invention consists of Caucasian individuals, the number of which is chosen based on how rare a haplotype is that one wants to be guaranteed to see. For example, if one wants to have a q % chance of not missing a haplotype that exists in the population at a p % frequency of occurring in the reference population, the number of individuals (n) who must be sampled is given by $2n=\log(1-q)/\log(1-p)$ where p and q are expressed as fractions. A preferred reference population allows the detection of any haplotype whose frequency is at least 10% with about 99% certainty. A particularly preferred reference population includes a 3-generation Caucasian family to serve as a control for checking quality of haplotyping procedures.

If the reference population comprises more than one ethnogeographic group, the frequency data for each group is examined to determine whether it is consistent with Hardy-Weinberg equilibrium. Hardy-Weinberg equilibrium (PRINCIPLES OF POPULATION GENOMICS, $3^{rd}$ ed., Hartl, Sinauer Associates, Sunderland, Mass., 1997) postulates that the frequency of finding the haplotype pair $H_1/H_2$ is equal to $p_{H\text{-}W}(H_1/H_2)=2p(H_1)p(H_2)$ if $H_1 \neq H_2$ and $p_{H\text{-}W}(H_1/H_2)=p(H_1)p(H_2)$ if $H_1=H_2$. A statistically significant difference between the observed and expected haplotype frequencies could be due to one or more factors including significant inbreeding in the population group, strong selective pressure on the gene, sampling bias, and/or errors in the genotyping process. If large deviations from Hardy-Weinberg equilibrium are observed in an ethnogeographic group, the number of individuals in that group can be increased to see if the deviation is due to a sampling bias. If a larger sample size does not reduce the difference between observed and expected haplotype pair frequencies, then one may wish to consider haplotyping the individual using a direct haplotyping method such as, for example, CLASPER System™ technology ((U.S. Pat. No. 5,866,404), single molecule dilution, or allele-specific long-range PCR (Michalotos-Beloin et al., *Nucleic Acids Res.* 24:4841-3 (1996)).

In one embodiment of this method for predicting a haplotype pair for an individual, the assigning step involves performing the following analysis. First, each of the possible haplotype pairs is compared to the haplotype pairs in the reference population. Generally, only one of the haplotype pairs in the reference population matches a possible haplotype pair and that pair is assigned to the individual. Occasionally, only one haplotype represented in the reference haplotype pairs is consistent with a possible haplotype pair for an individual, and in such cases the individual is assigned a haplotype pair containing this known haplotype and a new haplotype derived by subtracting the known haplotype from the possible haplotype pair. Alternatively, the haplotype pair in an individual may be predicted from the individual's genotype for that gene using reported methods (e.g., Clark et al., *Mol. Biol. Evol.* 7:111-22 (1990) or WO 01/80156) or through a commercial haplotyping service such as offered by Genaissance Pharmaceuticals, Inc. (New Haven, Conn.). In rare cases, either no haplotypes in the reference population are consistent with the possible haplotype pairs, or alternatively, multiple reference haplotype pairs are consistent with the possible haplotype pairs. In such cases, the individual is preferably haplotyped using a direct molecular haplotyping method such as, for example, CLASPER System™ technology (U.S. Pat. No. 5,866,404), SMD, or allele-specific long-range PCR (Michalotos-Beloin et al., supra).

Determination of the number of haplotypes present in the individual from the genotypes is illustrated here for haplotype (1) in Table 1. Table 3 below shows the 9 (3", where each of n bi-allelic polymorphic sites may have one of 3 different genotypes present) genotypes that may be detected at PS3 and PS4, using both chromosomal copies from an individual. 8 of the 9 possible genotypes for the two sites allow unambiguous determination of the number of copies of the haplotype (1) in Table 1 present in the individual. However, an individual with the G/A G/T genotype could possess one of the following genotype pairs: GG/AT, GT/AG, AG/GT, and AT/GG, and thus could have either one copy of haplotype (1) in Table 1 (GG/AT, AT/GG), or zero copies (GT/AG, AG/GT) of haplotype (1) in Table 1. For instances where there is ambiguity in the haplotype pair underlying the determined genotype (i.e., when two or more PSs are included in the haplotype), frequency information may be used to determine the most probable haplotype pair and therefore the most likely number of copies of the haplotype in the individual. If a particular haplotype pair consistent with the genotype of the individual is more frequent in the reference population than other pairs consistent with the genotype, then that haplotype pair with the highest frequency is the most likely to be present in the individual. The copy number of the haplotype of interest in this haplotype pair can then be determined by visual inspection of the alleles at the PS that comprise the response marker for each haplotype in the pair.

Alternatively, for the ambiguous genotypes, genotyping of one or more additional sites in CDK5 may be performed to eliminate the ambiguity in deconvoluting the haplotype pairs underlying the genotype at the particular PSs. The skilled artisan would recognize that alleles at these one or more additional sites would need to have sufficient linkage with the alleles in at least one of the possible haplotypes in the pair to permit unambiguous assignment of the haplotype pair. Although this illustration has been directed to the particular instance of determining the number of copies of haplotype (1) in Table 1 present in an individual, the process would be analogous for the other haplotypes shown in Table 1, or for the linked haplotypes or substitute haplotypes for any of the haplotypes in Table 1.

TABLE 3

Possible Copy Numbers of Haplotype (1) in Table 1 Based on Genotypes at PS3 and PS4

| PS3 | PS4 | Copy Number of Haploytpe (1) in Table 1 |
| --- | --- | --- |
| G/G | G/G | 2 |
| G/G | G/T | 1 |
| G/G | T/T | 0 |
| G/A | G/G | 1 |
| G/A | G/T | 1 or 0 |
| G/A | T/T | 0 |
| A/A | G/G | 0 |
| A/A | G/T | 0 |
| A/A | T/T | 0 |

The individual's genotype for the desired set of PS may be determined using a variety of methods well-known in the art. Such methods typically include isolating from the individual a genomic DNA sample comprising both copies of the gene or locus of interest, amplifying from the sample one or more target regions containing the polymorphic sites to be genotyped, and detecting the nucleotide pair present at each PS of interest in the amplified target region(s). It is not necessary to use the same procedure to determine the genotype for each PS of interest.

In addition, the identity of the allele(s) present at any of the novel PSs described herein may be indirectly determined by haplotyping or genotyping another PS having an allele that is in linkage disequilibrium with an allele of the PS that is of interest. PSs having an allele in linkage disequilibrium with an allele of the presently disclosed PSs may be located in regions of the gene or in other genomic regions not examined herein. Detection of the allele(s) present at a PS, wherein the allele is in linkage disequilibrium with an allele of the novel PSs described herein may be performed by, but is not limited to, any of the above-mentioned methods for detecting the identity of the allele at a PS.

Alternatively, the presence in an individual of a haplotype or haplotype pair for a set of PSs comprising a response marker may be determined by directly haplotyping at least one of the copies of the individual's genomic region of interest, or suitable fragment thereof, using methods known in the art. Such direct haplotyping methods typically involve treating a genomic nucleic acid sample isolated from the individual in a manner that produces a hemizygous DNA sample that only has one of the two "copies" of the individual's genomic region which, as readily understood by the skilled artisan, may be the same allele or different alleles, amplifying from the sample one or more target regions containing the PSs to be genotyped, and detecting the nucleotide present at each PS of interest in the amplified target region(s). The nucleic acid sample may be obtained using a variety of methods known in the art for preparing hemizygous DNA samples, which include: targeted in vivo cloning (TIVC) in yeast as described in WO 98/01573, U.S. Pat. No. 5,866,404, and 5,972,614; generating hemizygous DNA targets using an allele specific oligonucleotide in combination with primer extension and exonuclease degradation as described in U.S. Pat. No. 5,972,614; single molecule dilution (SMD) as described in Ruaño et al., *Proc. Natl. Acad. Sci.* 87:6296-300 (1990); and allele specific PCR (Ruaño et al., *Nucl. Acids Res.* 17:8392 (1989); Ruaño et al., *Nucl. Acids Res.* 19:6877-82 (1991); Michalatos-Beloin et al., supra).

As will be readily appreciated by those skilled in the art, any individual clone will typically only provide haplotype information on one of the two genomic copies present in an individual. If haplotype information is desired for the individual's other copy, additional clones will usually need to be examined. Typically, at least five clones should be examined to have more than a 90% probability of haplotyping both copies of the genomic locus in an individual. In some cases, however, once the haplotype for one genomic allele is directly determined, the haplotype for the other allele may be inferred if the individual has a known genotype for the PSs of interest or if the haplotype frequency or haplotype pair frequency for the individual's population group is known.

While direct haplotyping of both copies of the gene is preferably performed with each copy of the gene being placed in separate containers, it is also envisioned that direct haplotyping could be performed in the same container if the two copies are labeled with different tags, or are otherwise separately distinguishable or identifiable. For example, if first and second copies of the gene are labeled with different first and second fluorescent dyes, respectively, and an allele-specific oligonucleotide labeled with yet a third different fluorescent dye is used to assay the PS(s), then detecting a combination of the first and third dyes would identify the polymorphism in the first gene copy while detecting a combination of the second and third dyes would identify the polymorphism in the second gene copy.

The nucleic acid sample used in the above indirect and direct haplotyping methods is typically isolated from a biological sample taken from the individual, such as a blood sample or tissue sample. Suitable tissue samples include whole blood, saliva, tears, urine, skin and hair.

The target region(s) containing the PS of interest may be amplified using any oligonucleotide-directed amplification method, including but not limited to polymerase chain reaction (PCR) (U.S. Pat. No. 4,965,188), ligase chain reaction (LCR) (Barany et al., *Proc. Natl. Acad. Sci. USA* 88:189-93 (1991); WO 90/01069), and oligonucleotide ligation assay (OLA) (Landegren et al., *Science* 241:1077-80 (1988)). Other known nucleic acid amplification procedures may be used to amplify the target region(s) including transcription-based amplification systems (U.S. Pat. No. 5,130,238; European Patent No. EP 329,822; U.S. Pat. No. 5,169,766; WO 89/06700) and isothermal methods (Walker et al., *Proc. Natl. Acad. Sci. USA* 89:392-6 (1992)).

In both the direct and indirect haplotyping methods, the identity of a nucleotide (or nucleotide pair) at a PS(s) in the amplified target region may be determined by sequencing the amplified region(s) using conventional methods. If both copies of the gene are represented in the amplified target, it will be readily appreciated by the skilled artisan that only one nucleotide will be detected at a PS in individuals who are homozygous at that site, while two different nucleotides will be detected if the individual is heterozygous for that site. The polymorphism may be identified directly, known as positive-type identification, or by inference, referred to as negative-type identification. For example, where a polymorphism is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

A PS in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one PS may be detected at once using a set of allele-specific oligonucleotides or oligonucleotide pairs. Preferably, the members of the set have melting temperatures within 5° C., and more preferably within 2° C., of each other when hybridizing to each of the polymorphic sites being detected.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

Detecting the nucleotide or nucleotide pair at a PS of interest may also be determined using a mismatch detection technique, including but not limited to the RNase protection method using riboprobes (Winter et al., *Proc. Natl. Acad. Sci. USA* 82:7575 (1985); Meyers et al., *Science* 230:1242 (1985)) and proteins which recognize nucleotide mismatches, such as the *E. coli* mutS protein (Modrich, *Ann. Rev. Genet.* 25:229-53 (1991)). Alternatively, variant alleles can be identified by single strand conformation polymorphism (SSCP) analysis (Orita et al., *Genomics* 5:874-9 (1989); Humphries et al., in MOLECULAR DIAGNOSIS OF GENETIC DISEASES, Elles, ed., pp. 321-340, 1996) or denaturing gradient gel electrophoresis (DGGE) (Wartell et al., *Nucl. Acids Res.* 18:2699-706 (1990); Sheffield et al., *Proc. Natl. Acad. Sci. USA* 86:232-6 (1989)).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798. Another primer extension method is allele-specific PCR (Ruaño et al., 1989, supra; Ruaño et al., 1991, supra; WO 93/22456; Turki et al., *J. Clin. Invest.* 95:1635-41 (1995)). In addition, multiple PSs may be investigated by simultaneously amplifying multiple regions of the nucleic acid using sets of allele-specific primers as described in WO 89/10414.

The genotype or haplotype for the CDK5 gene of an individual may also be determined by hybridization of a nucleic acid sample containing one or both copies of the gene, mRNA, cDNA or fragment(s) thereof, to nucleic acid arrays and subarrays such as described in WO 95/11995. The arrays would contain a battery of allele-specific oligonucleotides representing each of the PSs to be included in the genotype or haplotype.

The invention also provides a kit for determining whether an individual has a response marker I, a response marker II, or a response marker III. The kit comprises a set of one or more oligonucleotides designed for identifying at least one of the alleles at each PS in a set of one or more PSs, wherein the set of one or more PSs comprises (a) PS3 and PS4; (b) PS2, PS3, and PS4; (c) a set of one or more PSs in a linked haplotype for any of haplotypes (1)-(2) in Table 1, or (d) a set of one or more PSs in a substitute haplotype for any of haplotypes (1)-(2) in Table 1. Preferably, the kit comprises a set of one or more oligonucleotides designed for identifying at least one of the alleles at each PS in a set of one or more PSs, wherein the set of one or more PSs is any of (a) PS3 and PS4; (b) PS2, PS3, and PS4; (c) a set of one or more PSs in a linked haplotype for any of haplotypes (1)-(2) in Table 1, and (d) a set of one or more PSs in a substitute haplotype for any of haplotypes (1)-(2) in Table 1.

In a preferred embodiment of the kit of the invention, the set of one or more oligonucleotides is designed for identifying both alleles at each PS in the set of one or more PSs. In another preferred embodiment, the individual is Caucasian. In another preferred embodiment, the kit further comprises a manual with instructions for (a) performing one or more reactions on a human nucleic acid sample to identify the allele or alleles present in the individual at each PS in the set of one or more PSs, and (b) determining if the individual has a response marker I, a response marker II, or a response marker III based on the identified allele or alleles. In another preferred embodiment, the linkage disequilibrium between a linked haplotype for any of haplotypes (1)-(2) in Table 1 and any of haplotypes (1)-(2) in Table 1 has a delta squared value selected from the group consisting of at least 0.75, at least 0.80, at least 0.85, at least 0.90, at least 0.95, and 1.0. In yet another preferred embodiment, the linkage disequilibrium between an allele at a substituting PS and an allele at a substituted PS for any of haplotypes (1)-(2) in Table 1 has a delta squared value selected from the group consisting of at least 0.75, at least 0.80, at least 0.85, at least 0.90, at least 0.95, and 1.0.

As used herein, an "oligonucleotide" is a probe or primer capable of hybridizing to a target region that contains, or that is located close to, a PS of interest. Preferably, the oligonucleotide has less than about 100 nucleotides. More preferably, the oligonucleotide is 10 to 35 nucleotides long. Even more preferably, the oligonucleotide is between 15 and 30, and most preferably, between 20 and 25 nucleotides in length. The exact length of the oligonucleotide will depend on the nature of the genomic region containing the PS as well as the genotyping assay to be performed and is readily determined by the skilled artisan.

The oligonucleotides used to practice the invention may be comprised of any phosphorylation state of ribonucleotides, deoxyribonucleotides, and acyclic nucleotide derivatives, and other functionally equivalent derivatives. Alternatively, oligonucleotides may have a phosphate-free backbone, which may be comprised of linkages such as carboxymethyl, acetamidate, carbamate, polyamide (peptide nucleic acid (PNA)) and the like (Varma, in MOLECULAR BIOLOGY AND BIOTECHNOLOGY, A COMPREHENSIVE DESK REFERENCE, Meyers, ed., pp. 617-20, VCH Publishers, Inc., 1995). Oligonucleotides of the invention may be prepared by chemical synthesis using any suitable methodology known in the art, or may be derived from a biological sample, for example, by restriction digestion. The oligonucleotides may be labeled, according to any technique known in the art, including use of radiolabels, fluorescent labels, enzymatic labels, proteins, haptens, antibodies, sequence tags and the like.

Oligonucleotides of the invention must be capable of specifically hybridizing to a target region of a polynucleotide containing a desired locus. As used herein, specific hybridization means the oligonucleotide forms an antiparallel double-stranded structure with the target region under certain hybridizing conditions, while failing to form such a structure when incubated with another region in the polynucleotide or with a polynucleotide lacking the desired locus under the same hybridizing conditions. Preferably, the oligonucleotide specifically hybridizes to the target region under conventional high stringency conditions.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, in MOLECULAR CLONING, A LABORATORY MANUAL, $2^{nd}$ ed., Sambrook et al., Cold Spring Harbor Press, Cold Spring Harbor, N.Y., 1989, and in NUCLEIC ACID HYBRIDIZATION, A PRACTICAL APPROACH, Haymes et al., IRL Press, Washington, D.C., 1985. While perfectly complementary oligonucleotides are preferred for detecting polymorphisms, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the probe or primer as long as the resulting probe or primer is still capable of specifically hybridizing to the target region.

Preferred oligonucleotides of the invention, useful in determining if an individual has a response marker I, a response marker II, or a response marker III, are allele-specific oligonucleotides. As used herein, the term allele-specific oligonucleotide (ASO) means an oligonucleotide that is able, under sufficiently stringent conditions, to hybridize specifically to one allele of a gene, or other locus, at a target region containing a PS while not hybridizing to the corresponding region in another allele(s). As understood by the skilled artisan, allele-specificity will depend upon a variety of readily optimized stringency conditions, including salt and formamide concentrations, as well as temperatures for both the hybridization and washing steps. Examples of hybridization and washing conditions typically used for ASO probes are found in Kogan et al., "Genetic Prediction of Hemophilia A" in PCR PROTOCOLS, A GUIDE TO METHODS AND APPLICATIONS, Academic Press, 1990, and Ruaño et al., Proc. Natl. Acad. Sci. USA 87:6296-300 (1990). Typically, an ASO will be perfectly complementary to one allele while containing a single mismatch for another allele.

Allele-specific oligonucleotides of the invention include ASO probes and ASO primers. ASO probes which usually provide good discrimination between different alleles are those in which a central position of the oligonucleotide probe aligns with the polymorphic site in the target region (e.g., approximately the $7^{th}$ or $8^{th}$ position in a 15 mer, the 8th or 9th position in a 16 mer, and the 10th or 11th position in a 20 mer). An ASO primer of the invention has a 3' terminal nucleotide, or preferably a 3' penultimate nucleotide, that is complementary to only one of the nucleotide alleles of a particular SNP, thereby acting as a primer for polymerase-mediated extension only if that nucleotide allele is present at the PS in the sample being genotyped. ASO probes and primers hybridizing to either the coding or noncoding strand are contemplated by the invention. ASO probes and primers listed below use the appropriate nucleotide symbol (R=G or A, Y=T or C, M=A or C, K=G or T, S=G or C, and W=A or T; WIPO standard ST.25) at the position of the PS to represent that the ASO contains either of the two alternative allelic variants observed at that PS.

A preferred ASO probe for detecting the alleles at each of PS2, PS3, and PS4, is listed in Table 4. Additionally, detection of the alleles at each of PS2, PS3, and PS4 could be accomplished by utilization of the complement of these ASO probes.

A preferred ASO forward and reverse primer for detecting the alleles at each of PS2, PS3, and PS4 is listed in Table 4.

TABLE 4

Preferred ASOs for Detecting Alleles at PSs in Haplotypes Comprising Preferred Embodiments of Response Markers I and Response Markers II[1]

| PS | ASO Probe Nucleotide sequence | SEQ ID NO. | ASO Forward Primer Nucleotide sequence | SEQ ID NO. | ASO Reverse Primer Nucleotide sequence | SEQ ID NO. |
|---|---|---|---|---|---|---|
| 2 | GGGCACAST TGCATG | 2 | GTTGCTGGGCA CAST | 5 | CCTGAACATG CAAST | 8 |
| 3 | AGAGTCCRT GGAGTT | 3 | GAGGGGAGAGT CCRT | 6 | GCTCAAAACT CCAYG | 9 |
| 4 | TGCAGCTKT GGCCCT | 4 | TGAAGATGCAG CTKT | 7 | TGGGAAAGGG CCAMA | 10 |

[1]These ASO probes and primers include the appropriate nucleotide symbol, Y = T or C, R = G or A, M = A or C, K =G or T/U, and S = G or C (World Intellectual Property Organization Handbook on Industrial Property Information and Documentation IPO Standard ST.25 (1998), Appendix 2, Table 1), at the position of the PS to represent that the ASO contains one of the two alternative polymorphisms observed at that position.

Other oligonucleotides useful in practicing the invention hybridize to a target region located one to several nucleotides downstream of a PS in a response marker. Such oligonucleotides are useful in polymerase-mediated primer-extension methods for detecting an allele at one of the PSs in the markers described herein and therefore such oligonucleotides are referred to herein as "primer-extension oligonucleotides." In a preferred embodiment, the 3'-terminus of a primer-extension oligonucleotide is a deoxynucleotide complementary to the nucleotide located immediately adjacent to the PS. A particularly preferred forward and reverse primer-extension oligonucleotide for detecting the alleles at each of PS2, PS3, and PS4 is listed in Table 5. Termination mixes are chosen to terminate extension of the oligonucleotide at the PS of interest, or one base thereafter, depending on the alternative nucleotides present at the PS.

TABLE 5

Preferred Primer Extension Oligos for Detecting Alleles at PSs in Haplotypes Comprising Preferred Embodiments of Response Markers I and Response Markers II

| | Forward Primer Extension | | Reverse Primer Extension | |
|---|---|---|---|---|
| PS | Sequence | SEQ ID NO. | Sequence | SEQ ID NO. |
| 2 | GCTGGGCACA | 11 | GAACATGCAA | 14 |
| 3 | GGGAGAGTCC | 12 | CAAAACTCCA | 15 |
| 4 | AGATGCAGCT | 13 | GAAAGGGCCA | 16 |

In some embodiments, the oligonucleotides in a kit of the invention have different labels to allow probing of the identity of nucleotides or nucleotide pairs at two or more PSs simultaneously.

The oligonucleotides in a kit of the invention may also be immobilized on or synthesized on a solid surface such as a microchip, bead, or glass slide (see, e.g., WO 98/20020 and WO 98/20019). Such immobilized oligonucleotides may be used in a variety of polymorphism detection assays, including but not limited to probe hybridization and polymerase extension assays. Immobilized oligonucleotides useful in practicing the invention may comprise an ordered array of oligonucleotides designed to rapidly screen a nucleic acid sample for polymorphisms in multiple genes at the same time.

Kits of the invention may also contain other components such as hybridization buffer (e.g., where the oligonucleotides are to be used as allele-specific probes) or dideoxynucleotide triphosphates (ddNTPs; e.g., where the alleles at the polymorphic sites are to be detected by primer extension). In a preferred embodiment, the set of oligonucleotides consists of primer-extension oligonucleotides. The kit may also contain a polymerase and a reaction buffer optimized for primer-extension mediated by the polymerase. Preferred kits may also include detection reagents, such as biotin- or fluorescent-tagged oligonucleotides or ddNTPs and/or an enzyme-labeled antibody and one or more substrates that generate a detectable signal when acted on by the enzyme. It will be understood by the skilled artisan that the set of oligonucleotides and reagents for performing the genotyping or haplotyping assay will be provided in separate receptacles placed in the container if appropriate to preserve biological or chemical activity and enable proper use in the assay.

In a particularly preferred embodiment, each of the oligonucleotides and all other reagents in the kit have been quality tested for optimal performance in an assay for determining the alleles at a set of PSs comprising a response marker I, a response marker II, or a response marker III.

In addition to the kits, the invention provides a method for predicting the cognitive response of an individual to treatment with a galantamine. The method comprises determining whether the individual has a response marker I, a response marker II, or a response marker III, and making a response prediction based on the results of the determining step. The determination of the response marker present in an individual can be made using one of the direct or indirect methods described herein. In some preferred embodiments, the determining step comprises identifying for one or both copies of the genomic locus present in the individual the identity of the nucleotide or nucleotide pair at the set of PSs comprising the selected response marker. Alternatively, the determining step may comprise consulting a data repository that states the individual's copy number for the haplotypes comprising one of the response markers I, response markers II, or response markers III. The data repository may be the individual's medical records or a medical data card. In preferred embodiments, the individual is Caucasian.

In some embodiments, if the individual is determined to have a response marker I, then the response prediction is that the individual is more likely to respond to galantamine than an individual having a response marker II or a response marker III, if the individual is determined to have a response marker II, then the response prediction is that the individual is less likely to respond to galantamine than an individual having a response marker I, but more likely to respond to galantamine than an individual having a response marker III, and if the individual is determined to have a response marker III, then the response prediction is that the individual is less likely to response to galantamine than an individual having a response marker I or a response marker II.

In other aspects, the invention provides an article of manufacture. In one embodiment, an article of manufacture comprises a pharmaceutical formulation and at least one indicium identifying a population for which the pharmaceutical formulation is indicated, wherein the identified population has a cognitive disorder. The pharmaceutical formulation comprises a galantamine compound as at least one active ingredient. Additionally, the pharmaceutical formulation may be regulated and the indicium may comprise the approved label for the pharmaceutical formulation. The identified population is partially or wholly defined by having a response marker I or a response marker II, wherein a trial population having a response marker I is more likely to respond to the formulation than a trial population lacking a response marker I, and a trial population having a response marker II is more likely to respond to the formulation than a trial population lacking both a response marker I and a response marker II. The identified population preferably may be further defined as Caucasian. A population wholly defined by having a response marker I or a response marker II is one for which there are no other factors which should be considered in identifying the population for which the pharmaceutical formulation is indicated. In contrast, a population that is partially defined by having a response marker I or a response marker II is one for which other factors may be pertinent to identification of the population for which the pharmaceutical formulation is indicated. Examples of other such factors are age, weight, gender, disease state, possession of other genetic markers or biomarkers, or the like. The cognitive disorder can include mild or moderate dementia of the Alzheimer's type, and dementia associated with Parkinson's Disease.

The pharmaceutical formulation may be formulated, in any way known in the art, for any mode of delivery (i.e., oral), and any mode of release (i.e., sustained release). In some embodiments, the pharmaceutical formulation is a tablet or capsule and the article may further comprise an additional indicium comprising the color or shape of the table or capsule. In other embodiments, the article may further comprise an additional indicium comprising a symbol stamped on the tablet or capsule, or a symbol or logo printed on the approved label.

In some embodiments of this article, the approved label may comprise a statement about the identified population. In some or all of these embodiments, the label may describe the change in cognitive function expected for the identified population. Additionally, in some or all of these embodiments, a galantamine is present in the pharmaceutical formulation at an amount effective to improve cognitive function in the identified population. The galantamine compound that is present in the pharmaceutical formulation is selected from galantamine, a galantamine derivative, and pharmaceutically acceptable salts of galantamine or the galantamine derivative. Various galantamine derivatives have been reported to be useful for treating Alzheimer's and related dementias, including but not limited to the compounds described and claimed in U.S. Pat. Nos. 6,150,354, 6,268,358, 6,319,919 B1, 6,323,196, and 6,326,196; and the compounds described and claimed in European Patent Application No. EP 236684. Pharmaceutically acceptable salts of galantamine reported to be useful in treating Alzheimer's disease and related dementias include those described in U.S. Pat. Nos. 4,663,318 and 6,358,941, as well as WO 00/38686. In preferred embodiments, the galantamine compound is galantamine hydrobromide.

An additional embodiment of the article of manufacture provided by the invention comprises packaging material and a pharmaceutical formulation contained within said packaging material. The pharmaceutical formulation comprises a galantamine compound as at least one active ingredient. The packaging material may comprise a label stating that the pharmaceutical formulation is indicated for a population having a cognitive disorder, wherein the population is partly or wholly defined by having a response marker I or a response marker II. The indicated population preferably may be further defined as Caucasian. The label may further state that a specified test can be used to identify members of the indicated population. Preferably the specified test is a genetic test. The cognitive disorder can include mild or moderate dementia of the Alzheimer's type, and dementia associated with Parkinson's Disease.

Additionally, in other aspects of the invention, a method of manufacturing a drug product comprising a galantamine compound as at least one active ingredient is provided. The method comprises combining in a package a pharmaceutical formulation comprising the galantamine compound and a label that states that the formulation is indicated for a population having a cognitive disorder, wherein the population is partially or wholly defined by having a response marker I or a response marker II, wherein a trial population having a response marker I is more likely to respond to the formulation than a trial population lacking a response marker I, and a trial population having a response marker II is more likely to respond to the formulation than a trial population lacking both a response marker I and a response marker II. The indicated population may be identified on the pharmaceutical formulation, on the label or on the package by at least one indicium, such as a symbol or logo, color, or the like. The indicated population preferably may be further defined as Caucasian. The cognitive disorder can include mild or moderate dementia of the Alzheimer's type, and dementia associated with Parkinson's Disease. The galantamine compound is selected from galantamine, a galantamine derivative, and pharmaceutically acceptable salts of galantamine or the galantamine derivative.

Detecting the presence of a response marker I, a response marker II, or a response marker III in an individual is also useful in a method for seeking regulatory approval for marketing a pharmaceutical formulation for improving cognitive function in a population having a cognitive disorder, wherein the population is partially or wholly defined by having a response marker I or a response marker II. The method comprises conducting at least one clinical trial which comprises administering the pharmaceutical formulation and a placebo to each of a first, second, third, and fourth treatment group of individuals having a cognitive disorder, wherein each individual in the first treatment group has a response marker I, each individual in the second treatment group lacks a response marker I, each individual in the third treatment group has a response marker II, and each individual in the fourth treatment group has a response marker III, demonstrating that the first treatment group is more likely to respond to the pharmaceutical formulation than the second treatment group, demonstrating that the third treatment group is more likely to respond to the pharmaceutical formulation than the fourth treatment group, and filing with a regulatory agency an application for marketing approval of the pharmaceutical formulation with a label stating that the pharmaceutical formulation is indicated for a population having a cognitive disorder, and further stating that individuals having a response marker I are more likely to respond to the pharmaceutical formulation than individuals having a response marker II or a response marker III, and that individuals having a response marker II are more likely to respond to the pharmaceutical formulation than individuals having a response marker III. In preferred embodiments, the regulatory agency is the United States Food and Drug Administration (FDA) or the European Agency for the Evaluation of Medicinal Products (EMEA), or a future equivalent of these agencies.

The clinical trial may be conducted by recruiting individuals having a cognitive disorder, determining whether or not they have a response marker I, a response marker II, or a response marker III, and assigning them to the first, second, third, and fourth treatment groups based on the results of the determining step. The individuals in each treatment group are preferably administered the same dose of the pharmaceutical formulation, which includes, as at least one active ingredient, a compound effective in improving cognitive function, such as a galantamine compound, including galantamine, a galantamine derivative, and pharmaceutically acceptable salts of galantamine or the galantamine derivative. The pharmaceutical formulation may contain other active ingredients, for example another compound known or believed to be effective in improving cognitive function. The cognitive disorder can include mild or moderate dementia of the Alzheimer's type, and dementia associated with Parkinson's Disease.

The regulatory agency may be any person or group authorized by the government of a country anywhere in the world to control the marketing or distribution of drugs in that country. Preferably, the regulatory agency is authorized by the government of a major industrialized country, such as Australia, Canada, China, a member of the European Union, Japan, and the like. Most preferably the regulatory agency is authorized by the government of the United States and the type of application for approval that is filed will depend on the legal requirements set forth in the last enacted version of the Food, Drug and Cosmetic Act that are applicable for the pharmaceutical formulation and may also include other considerations such as the cost of making the regulatory filing and the marketing strategy for the composition. For example, if the pharmaceutical formulation has previously been approved for the same cognitive function, then the application might be a paper NDA, a supplemental NDA or an abbreviated NDA, but the application would be a full NDA if the pharmaceutical formulation has never been approved before; with these terms having the meanings applied to them by those skilled in the pharmaceutical arts or as defined in the Drug Price Competition and Patent Term Restoration Act of 1984.

Additionally, in other aspects of the invention, there is provided a method for marketing a drug product comprising promoting to a target audience the use of a drug product for improving cognitive function in a population having a cognitive disorder, wherein the population is partially or wholly defined by having a response marker I or a response marker II, wherein the drug product comprises a compound effective in improving cognitive function, and wherein a trial population having a response marker I are more likely to respond to the drug product than a trial population lacking a response marker I, and a trial population having a response marker II are more likely to respond to the drug product than a trial population lacking both a response marker I and a response marker III. The drug product can comprise any compound effective in improving cognitive function, such as a galantamine compound, including galantamine, a galantamine derivative, and pharmaceutically acceptable salts of galantamine or the galantamine derivative. The target audience can be members of a group that is in position to influence prescription or purchase of the drug product. Such groups include physicians, pharmacists, insurance companies and health maintenance organizations, individuals at risk for developing AD, and government agencies such as those involved in providing or regulating medical insurance and those involved in regulating the marketing of drugs.

The promoting step can employ printed publications such as medical journals and consumer magazines, radio and television advertisements, and public presentations such as presentations at medical and scientific conferences. In a preferred embodiment, the drug product is approved for marketing to delay the onset of AD in the population, and the promoting step includes a statement that relates the approved drug product to its appearance, e.g., the color or shape of a tablet or capsule formulation, or some design stamped or embossed thereon.

In practicing any of the embodiments of the invention that are described herein, determination of the therapeutically effective dose of a galantamine compound and/or the appropriate route of administration is well within the capability of those skilled in the art. For example, the dose can be estimated initially either in cell culture assays or in an animal model of the cognitive disorder. Such information may then be used to determine the approximate concentration range and route of administration for humans. The exact dosage will be determined by the practitioner, in light of factors relating to the patient requiring treatment, including but not limited to severity of the disease state, general health, age, weight and gender of the patient, diet, time and frequency of administration, other drugs being taken by the patient, and tolerance/response to the treatment.

One known animal model for Alzheimer's disease in humans is described in Haroutunian et al., *Life Sciences* 37:945-52 (1985). This rat model has a selective lesion placed in a subcortical nucleus (nucleus basalis of Meynert), which results in a cortical cholinergic deficiency, similar in magnitude to that seen in early to moderate stage Alzheimer's disease. Numerous behavioral deficits, including the inability to learn and retain new information, characterizes this lesion. Drugs that can normalize these abnormalities would have a reasonable expectation of efficacy in Alzheimer's disease.

The galantamine compound or composition used in practicing the invention may be administered to a patient orally or by subcutaneous or intravenous injection. Sustained release delivery mechanisms may be particularly useful, for example, intracerebroventricularly by means of an implanted reservoir by use of sustained release capsules or by means of a transdermal patch. It may be necessary to begin at lower doses than are ultimately effective.

Certain galantamine compounds used in practicing different embodiments of the invention may be only sparingly soluble in water at room temperature and so injectable compositions are normally in the form of an aqueous suspension. If necessary, pharmaceutically-acceptable suspension aids may be employed. Typically, such a suspension will be employed at a concentration of 1-50 mg/ml more commonly 5-40 mg/ml, for example, 5-30 mg/ml or 10-40 mg/ml, typically 20-30 mg/ml of the galantamine compound of interest.

Typical dosage rates when administering a galantamine compound will depend upon the activity of the compound and the exact nature and condition of the patient. For example, typical dosage rates for administration by injection are in the range 5-1,000 mg per day depending upon the patient. In some cases, even lower dosages such as 0.5 or 1 mg per day may be helpful. For example, divided doses in the range 0.5-5 mg/kg body weight per day may prove useful. Typically, one might administer a dosage of 50-300 mg per day to a patient of a body weight of 40-100 kg, although in appropriate cases such dosages may prove useful for patients having a body weight outside this range. In other cases, dosages as low as 0.1 mg and as high as 500 mg may be appropriate for persons in this body weight range.

Galantamine compounds used in practicing the invention may also be administered orally, for example, as an aqueous suspension or a solution in aqueous ethanol or as a solid such as a tablet or capsule. Suspensions or solutions for oral administration are typically of about the same concentration as those used for injections. However, it may be desirable when administering the drug orally to use a higher dosage rate than when administering it by injection. For example, dosages up to 200 mg per day may be used, such as dosages in the range 10-60 mg per day. In preparing such tablets or capsules, standard tablet or capsule-making techniques may be employed. The dosage rate of the compound of the invention or its pharmaceutically-acceptable salt will normally be in the same range as for oral administration of a liquid. If desired, a pharmaceutically-acceptable carrier such as starch or lactose may be used in preparing tablets. Capsules may be prepared using soft gelatin as the encapsulating agent. If desired, such capsules may be in the form of sustained release capsules wherein the main capsule contains microcapsules of active compound which release the contents over a period of several hours thereby maintaining a constant level of active compound in the patient's blood stream.

The following specific formulations may find use in practicing one or more embodiments of the present invention: (1) Tablets or capsules containing 0.1, 0.5, 1.0, 5, 10 and 25 mg of the hydrobromide salt of galantamine or a galantamine derivative to be taken four times a day, or a sustained-release-preparation delivering an equivalent daily dose; (2) a parenteral solution containing 5 mg/ml of the galantamine compound; and (3) a liquid formulation for oral administration available in 5 mg/5 ml and 25 mg/5 ml concentration.

There have been reports that galantamine can cause cardiac arrhythmias. If such problems are believed to be a risk when practicing an embodiment of the present invention, it may be desirable to administer the galantamine compound in conjunction with another drug such as propantheline bromide to control such arrhythmias. Since other side effects, such as nausea, are common with drugs that act on the central nervous system, a galantamine compound or composition used in the present invention may be administered in conjunction with an agent for control of such side effects.

Further, in performing any of the methods described herein which require information on the haplotype content of the individual (i.e., the haplotypes and haplotype copy number present in the individual for the polymorphic sites in haplotypes comprising a response marker I, a response marker II, or a response marker III) or which require knowing if a response marker I, a response marker II, or a response marker III is present in the individual, the individual's CDK5 haplotype content or response marker may be determined by consulting a data repository such as the individual's patient records, a medical data card, a file (e.g., a flat ASCII file) accessible by a computer or other electronic or non-electronic media on which information about the individual's CDK5 haplotype content or response marker can be stored. As used herein, a medical data card is a portable storage device such as a magnetic data card, a smart card, which has an on-board processing unit and which is sold by vendors such as Siemens of Munich Germany, or a flash-memory card. The medical data card may be, but does not have to be, credit-card sized so that it easily fits into pocketbooks, wallets and other such objects carried by the individual. The medical data card may be swiped through a device designed to access information stored on the data card. In an alternative embodiment, portable data storage devices other than data cards can be used. For example, a touch-memory device, such as the "i-button" produced by Dallas Semiconductor of Dallas, Tex. can store information about an individual's CDK5 haplotype content or response marker, and this device can be incorporated into objects such as jewelry. The data storage device may be implemented so that it can wirelessly communicate with routing/intelligence devices through IEEE 802.11 wireless networking technology or through other methods well known to the skilled artisan. Further, as stated above, information about an individual's haplotype content or response marker can also be stored in a file accessible by a computer; such files may be located on various media, including: a server, a client, a hard disk, a CD, a DVD, a personal digital assistant such as a Palm Pilot, a tape, a zip disk, the computer's internal ROM (read-only-memory) or the internet or worldwide web. Other media for the storage of files accessible by a computer will be obvious to one skilled in the art.

Any or all analytical and mathematical operations involved in practicing the methods of the present invention may be implemented by a computer. For example, the computer may execute a program that assigns CDK5 haplotype pairs and/or a response marker I, a response marker II, or a response marker III to individuals based on genotype data inputted by a laboratory technician or treating physician. In addition, the computer may output the predicted change in cognitive function in response to a galantamine following input of the individual's CDK5 haplotype content or response marker, which was either determined by the computer program or input by the technician or physician. Data on which response markers were detected in an individual may be stored as part of a relational database (e.g., an instance of an Oracle database or a set of ASCII flat files) containing other clinical and/or haplotype data for the individual. These data may be stored on the computer's hard drive or may, for example, be stored on a CD ROM or on one or more other storage devices accessible by the computer. For example, the data may be stored on one or more databases in communication with the computer via a network.

It is also contemplated that the above described methods and compositions of the invention may be utilized in combination with identifying genotype(s) and/or haplotype(s) for other genomic regions.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples.

EXAMPLES

The Examples herein are meant to exemplify the various aspects of carrying out the invention and are not intended to limit the scope of the invention in any way. The Examples do not include detailed descriptions for conventional methods employed, such as in the synthesis of oligonucleotides or polymerase chain reaction. Such methods are well known to those skilled in the art and are described in numerous publications, for example, MOLECULAR CLONING: A LABORATORY MANUAL, $2^{nd}$ ed., supra.

Example 1

This example illustrates the clinical and biochemical characterization of selected individuals in a cohort of 449 Caucasian patients diagnosed with Alzheimer's Disease.

The patient cohort was selected from patients participating in three clinical trials of galantamine held internationally and in the United States (GAL-INT2, GAL-USA 10, and GAL-INT-1) (Rockwood et al., supra; Tariot et al., supra; Wilcock et al., supra), and a fourth clinical trial with a similar disease population. In brief, the galantamine trials were carried out by delivering to patients galantamine at daily dosages of 8 mg, 16 mg, 24 mg, or 32 mg depending on the trial. Following 3, 5, 6 or 12 months of treatment in the GAL-INT2, GAL-USA 10, GAL-INT-1 and SAB-USA-25 trials, respectively, the severity of symptoms in patients were evaluated using the cognitive subscale of the Alzheimer's Disease Assessment Scale (ADAS-cog) (Rosen et al., supra; Rockwood et al., supra; Tariot et al., supra; Wilcock et al., supra). The ADAS-cog measures cognitive function, including spoken language ability, comprehension of spoken language, recall of test instructions, word-finding difficulty in spontaneous speech, following commands, naming objects and fingers, constructional praxis, ideational praxis, orientation, word-recall task and word-recognition task (*Alzheimer's Insights Online*, supra).

For the clinical association study described in Example 2 below, 174 patients were selected and used to populate two groups in a tailed sampling strategy, intended to enrich alleles correlating with drug response in the population. This population consisted of 85 responders and 89 non-responders. Patients were assigned to responder and non-responder groups based on having a change in ADAS-cog score (ΔADAS-cog) that met a cut-off value that was chosen based on the differences in treatment times in the four clinical trials described above. The ΔADAS-cog cut-off values and treatment times used for each responder and non-responder group from each of the four clinical trials are shown in Table 6 below.

TABLE 6

ΔADAS-cog Used to Select Patients for Responder and Non-Responder Groups

| Clinical Trial | Treatment Time (months) | Responder | Non-responder |
|---|---|---|---|
| GAL-INT-2 | 3 | Δ ≦ −5 | Δ ≧ 2 |
| GAL-USA-10 | 5 | Δ ≦ −7 | Δ ≧ 3 |
| GAL-INT-1 | 6 | Δ ≦ −7 | Δ ≧ 3 |
| SAB-USA-25 | 12 | Δ ≦ −3 | N/A |

Table 7 below shows the number of patients from each of the four clinical trials that were placed in each of the clinical association analyses groups.

TABLE 7

| Trial Name (Number of Patients) | Composition of the Treatment Group | | |
|---|---|---|---|
| | Treatment Group | | |
| | Responder | Non-Responder | Total |
| GALINT1 | 0 | 0 | 0 |
| GALINT2 | 4 | 1 | 5 |
| GALUSA10 | 81 | 88 | 169 |
| SABUSA25 | 0 | 0 | 0 |
| TOTAL | 85 | 89 | 174 |

Example 2

This example illustrates genotyping of the patient cohort for the four CDK5 polymorphic sites selected by the inventors herein for analysis.

Genomic DNA samples were isolated from blood samples obtained from each member of the cohort and genotyped at each of PS1-PS4 (Table 2) using the MassARRAY technology licensed from Sequenom (San Diego, Calif.). In brief, this genotyping technology involves performing a homogeneous MassEXTEND assay (hME), in which an initial polymerase chain reaction is followed by an allele-specific oligonucleotide extension reaction in the same tube or plate well, and then detecting the extended oligonucleotide by MALDI-TOF mass spectrometry.

For each of the four CDK5 polymorphic sites of interest, a genomic DNA sample was amplified in a 8.0 μL multiplexed PCR reaction consisting of 2.5 ng genomic DNA (0.3 ng/μL), 0.85 μL 10× reaction buffer, 0.32 units Taq Polymerase, up to five sets of 0.4 pmol each of forward PCR primer (5' to 3') and reverse PCR primer (3' to 5') and 1.6 nmol each of dATP, dCTP, dGTP and dTTP. A total of four reactions were performed comprising the following polymorphic site groups: (1) PS1; (2) PS2; (3) PS3; and (4) PS4. Forward and Reverse PCR primers used for each of the four CDK5 polymorphic sites consisted of a 10 base universal tag (5'-AGCGGATAAC-3'; SEQ ID NO:17) followed by one of the CDK5-specific sequences shown in Tables 8A and 8B below:

TABLE 8A

Forward PCR CDK5-specific Primer Secquences used in hME Assays

| | | |
|---|---|---|
| PS1 | AGCGGATAACTTCTACCGCGGAGGCAAAC | (SEQ ID NO:18) |
| PS2 | AGCGGATAACAATGACTGGGAGGAGAGAGG | (SEQ ID NO:19) |
| PS3 | AGCGGATAACATCACTGCCCTCACCCATTG | (SEQ ID NO:20) |
| PS4 | AGCGGATAACCTCACCCTGCCCCTGAAGAT | (SEQ ID NO:21) |

TABLE 8B

Reverse PCR CDK5-specific Primer Secquences used in hME Assays

| | | |
|---|---|---|
| PS1 | AGCGGATAACAAACGGACACGCGTTGCTTC | (SEQ ID NO:22) |
| PS2 | AGCGGATAACAACCAGGTGCTGAAAGGTGG | (SEQ ID NO:23) |
| PS3 | AGCGGATAACTATCCTTGCTTTCCTCTGCC | (SEQ ID NO:24) |
| PS4 | AGCGGATAACGGAGTCAAGGATCACTTGGG | (SEQ ID NO:25) |

PCR thermocycling conditions were: initial denaturation of 95° C. for 15 minutes followed by 45 cycles of 94° C. for 20 seconds, 56° C. for 30 seconds and 72° C. for 1 minute followed by a final extension of 72° C. for 3 minutes. Following the final extension, unincorporated deoxynucleotides were degraded by adding 0.48 units of Shrimp Alkaline Phosphatase (SAP) to the PCR reactions and incubation for 20 minutes at 37° C. followed by 5 minutes at 85° C. to inactivate the SAP.

Template-dependent primer extension reactions were then performed on the multiplexed PCR products by adding a 2.0 µL volume of an hME cocktail consisting of 720 pmol each of three dideoxynucleotides and 720 pmol of one deoxynucleotide, 8.6 pmol of an extension primer, 0.2 µL of 5× Thermosequenase Reaction Buffer, and NanoPure grade water. The thermocycling conditions for the mass extension reaction were: initial denaturation for 2 minutes at 94° C. followed by 40 cycles of 94° C. for 5 seconds, 40° C. for 5 seconds and 72° C. for 5 seconds. Extension primers used to genotype each of the four CDK5 polymorphic sites are shown in Table 9 below:

TABLE 9

Extension Primers for Genotyping CDK5 Polymorphic Sites

| | | |
|---|---|---|
| PS1 | GGAGGCAAACCTTGGACTTCAA | (SEQ ID NO:26) |
| PS2 | TCAGACGCCCTGAACATGCAA | (SEQ ID NO:27) |
| PS3 | TCACCCATTGTGCTCAAAACTCCA | (SEQ ID NO:28) |
| PS4 | CCCCTGAAGATGCAGCT | (SEQ ID NO:29) |

The extension products were desalted prior to analysis by mass spectrometry by mixing them with AG50×8 NH$_4$OAc cation exchange resin.

The desalted multiplexed extension products were applied onto a SpectroCHIP™ using the SpectroPOINT™ 24 pin applicator tool as per manufacturer's instructions (Sequenom Industrial Genomics, Inc. San Diego, Calif.). The SpectroChip™ was loaded into a Bruker Biflex III™ linear time-of flight mass spectrometer equipped with a SCOUT 384 ion source and data was acquired using XACQ 4.0, MOCTL 2.1, AutoXecute 4.2 and XMASS/XTOF 5.0.1 software on an Ultra 5™ work station (Sun Microsystems, Palo Alto Calif.). Mass spectrometry data was subsequently analyzed on a PC running Windows NT 4.0 (Microsoft, Seattle Wash.) with SpectroTYPER™ genotype calling software (Sequenom Industrial Genomics, Inc. San Diego, Calif.).

Example 3

This example illustrates the deduction of haplotypes from the CDK5 genotyping data generated in Example 2.

Haplotypes were estimated from the unphased genotypes using a computer-implemented algorithm for assigning haplotypes to unrelated individuals in a population sample, essentially as described in WO 01/80156 (Genaissance Pharmaceuticals, Inc., New Haven, Conn.). In this method, haplotypes are assigned directly from individuals who are homozygous at all sites or heterozygous at no more than one of the variable sites. This list of haplotypes is then used to deconvolute the unphased genotypes in the remaining (multiply heterozygous) individuals.

A quality control analysis was performed on the deduced haplotypes, which included analysis of the frequencies of the haplotypes and individual SNPs therein for compliance with principles of Hardy-Weinberg equilibrium.

Example 4

This example illustrates analysis of the CDK5 haplotypes in Table 1 for association with individuals' responses to galantamine.

The statistical analyses compared ΔADAS-cog in patients with one copy vs. zero copies, two copies vs. zero copies, and two copies vs. one copy (within a patient's genome) of a particular allele, using a logistic regression analysis on two-degrees of freedom to associate clinical response with a particular haplotype. The following covariates were also included: age, gender, history, smoking, ADAS-cog baseline, dose (BID), body mass index, and CYP2D6. The logistic regression included assessment of associations between the haplotypes and the binary outcome of clinical response.

For the results obtained on the analyses, adjustments were made for multiple comparisons, using a permutation test (MULTIVARIATE PERMUTATION TESTS: WITH APPLICATIONS IN BIOSTATISTICS, Pesarin, John Wiley and Sons, New York, 2001). In this test, a sub-haplotype's data for each observation were kept constant, while all the remaining variables (outcome and covariates) were randomly permuted so that covariates always stayed with the same outcome. The permutation model was fitted for each of the several haplotypes, and the lowest p-value was kept. In total, 1000 permutations were done. Two CDK5 haplotypes of at least one polymorphism were identified that show a correlation with an individual's ability to respond to galantamine. These CDK5 haplotypes are shown above in Table 1, and the unadjusted ("raw") and adjusted ("perm.") p-values for these two haplotypes are shown below in Tables 10A, 10B, and 10C.

TABLE 10A

CDK5 Haplotypes Having Association with Response to Galantamine (1 vs. 0 copies)

| Haplotype | Perm. p | Raw p | Subject Count for Haplotype (# of copies) | Subject Count for Haplotype with Highest Level Response (# of copies) | Odds Ratio (O.R.) | Lower Confidence Interval (C.I.) of O.R. | Upper C.I. of O.R. |
|---|---|---|---|---|---|---|---|
| (1) | 0.012 | 0.002477 | 88 (1) 41 (0) | 46 (1) 26 (0) | 0.5067927 | 0.2248439 | 1.1422984 |
| (2) | 0.012 | 0.002477 | 88 (1) 41 (0) | 46 (1) 26 (0) | 0.5067927 | 0.2248439 | 1.1422984 |

TABLE 10B

CDK5 Haplotypes Having Association with Response to Galantamine (2 vs. 0 copies)

| Haplotype | Perm. p | Raw p | Subject Count for Haplotype (# of copies) | Subject Count for Haplotype with Highest Level Response (# of copies) | Odds Ratio (O.R.) | Lower Confidence Interval (C.I.) of O.R. | Upper C.I. of O.R. |
|---|---|---|---|---|---|---|---|
| (1) | 0.012 | 0.002477 | 45 (2) 41 (0) | 13 (2) 26 (0) | 0.183118 | 0.0695317 | 0.4822576 |
| (2) | 0.012 | 0.002477 | 45 (2) 41 (0) | 13 (2) 26 (0) | 0.183118 | 0.0695317 | 0.4822576 |

TABLE 10C

CDK5 Haplotypes Having Association with Response to Galantamine (2 vs. 1 copies)

| Haplotype | Perm. p | Raw p | Subject Count for Haplotype (# of copies) | Subject Count for Haplotype with Highest Level Response (# of copies) | Odds Ratio (O.R.) | Lower Confidence Interval (C.I.) of O.R. | Upper C.I. of O.R. |
|---|---|---|---|---|---|---|---|
| (1) | 0.012 | 0.002477 | 45 (2) 88 (1) | 13 (2) 46 (1) | 0.3613272 | 0.1581388 | 1.8255869 |
| (2) | 0.012 | 0.002477 | 45 (2) 88 (1) | 13 (2) 46 (1) | 0.3613272 | 0.1581388 | 1.8255869 |

As seen in Tables 10A, 10B, and 10C, each of haplotypes (1) and (2) shows a correlation with an individual's response to galantamine. The odds ratio (O.R.) column for Table 10A indicates the likelihood that an individual with one copy of haplotype (1) or haplotype (2) will respond to galantamine as compared to an individual with zero copies of haplotype (1) or haplotype (2), wherein an O.R. greater than 1 indicates that an individual with one copy is more likely to respond than an individual with zero copies, and an O.R. less than 1 indicates that an individual with one copy is less likely to respond than an individual with zero copies. The O.R. column for Table 10B indicates the likelihood that an individual with two copies of haplotype (1) or haplotype (2) will respond to galantamine as compared to an individual with zero copies of haplotype (1) or haplotype (2), wherein an O.R. greater than 1 indicates that an individual with two copies is more likely to respond than an individual with zero copies, and an O.R. less than 1 indicates that an individual with two copies is less likely to respond than an individual with zero copies. The O.R. column for Table 10C indicates the likelihood that an individual with two copies of haplotype (1) or haplotype (2) will respond to galantamine as compared to an individual with one copy of haplotype (1) or haplotype (2), wherein an O.R. greater than 1 indicates that an individual with two copies is more likely to respond than an individual with one copy, and an O.R. less than 1 indicates that an individual with two copies is less likely to respond than an individual with one copy.

In summary, the study described herein identified CDK5 haplotypes that are correlated with the likelihood of whether an individual will exhibit a cognitive response to galantamine. It is believed that such information will be useful to physicians in deciding whether a patient should be prescribed galantamine for treating AD and other diseases that cause dementia or cognitive impairment, in performing clinical trials of galantamine and derivatives thereof, and in obtaining marketing approval of galantamine for treating diseases that cause cognitive impairment.

In view of the above, it will be seen that the several advantages of the invention are achieved and other advantageous results attained. As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated in their entirety by reference. The discussion of references herein is intended merely to summarize the assertions made by their authors and no admission is made that any reference constitutes prior art. Applicants reserve the right to challenge the accuracy and pertinence of the cited references.

What is claimed is:

1. A method for determining whether an individual has a galantamine response marker I, a galantamine response marker II, or a galantamine response marker III in said individual's cyclin-dependent kinase 5 (CDK5) gene, the method comprising:

determining whether the individual has zero copies, one copy, or two copies of any of (a) haplotype (1), (b) a linked haplotype for haplotype (1), and (c) a substitute haplotype for haplotype (1), wherein haplotype (1) has a G at polymorphic sites (PSs) 3 and 4 of the CDK5 gene (SEQ ID NO:1), and wherein polymorphic site (PS) 3 is at nucleotide position 4808 and PS4 is at nucleotide position 5284 of SEQ ID NO:1, wherein the individual has a galantamine response marker I if the individual has zero copies of any of (a) said haplotype (1), (b) said linked haplotype for haplotype (1), and (c) said substitute haplotype for haplotype (1), the individual has a galantamine response marker II if the individual has one copy of any of (a) said haplotype (1), (b) said linked haplotype for haplotype (1), and (c) said substitute haplotype for haplotype (1), and the individual has a galantamine response marker III if the individual has two copies of any of (a) said haplotype (1), (b) said linked haplotype for haplotype (1), and (c) said substitute haplotype for haplotype (1).

2. The method of claim 1, wherein said determining comprises obtaining the individual's genotype for least one PS in the set of PSs that comprises (a) said haplotypes (1); (b) said linked haplotype for haplotypes (1); or (c) said substitute haplotype for haplotypes (1).

3. The method of claim 2, wherein the individual's genotype for the set of PSs is obtained by any of (a) a primer extension assay; (b) an allele-specific PCR assay; (c) a nucleic acid amplification assay; (d) a hybridization assay; (e) a mismatch-detection assay; (f) an enzymatic nucleic acid cleavage assay; and (g) a sequencing assay.

4. The method of claim 1, wherein the determining comprises consulting a data repository that provides information on the individual's copy number for haplotypes (1), a linked haplotype for haplotypes (1), or a substitute haplotype for haplotype (1).

5. The method of claim 4, wherein the data repository is the individual's medical records or a medical data card.

6. The method of claim 1 or claim 2, wherein the method comprises determining whether an individual has zero copies, one copy, or two copies of said haplotype (1).

7. The method of claim 1, wherein the linkage disequilibrium between the linked haplotype and haplotypes (1) has a delta squared value selected from the group consisting of at least 0.75, at least 0.80, at least 0.85, at least 0.90, at least 0.95, and 1.0.

8. The method of claim 7, wherein the linkage disequilibrium between the linked haplotype and haplotype (1) has a delta squared value of at least 0.95.

9. The method of claim 1, wherein the linkage disequilibrium between the allele at a substituting PS in the substitute haplotype and the allele at a substituted PS in haplotypes (1) has a delta squared value selected from the group consisting of at least 0.75, least 0.80, at least 0.85, at least 0.90, at least 0.95, and 1.0.

10. The method of claim 9, wherein the linkage disequilibrium between the allele at a substituting PS and the allele at a substituted PS in haplotype (1) in Table 1 has a delta squared value of at least 0.95.

11. The method of claim 1, wherein the individual is Caucasian.

12. The method of claim 1, wherein the individual is diagnosed as having a cognitive disorder.

13. The method of claim 1, wherein the individual is a candidate for treatment with a galantamine compound.

14. A method for assigning an individual to a first galantamine response marker group, a second galantamine response marker group, or a third galantamine response marker group based on the galantamine response marker present in said individual's cyclin-dependent kinase 5 (CDK5) gene, the method comprising:
    determining whether the individual has zero copies, one copy, or two copies of any of (a) haplotype (1), (b) a linked haplotype for haplotype (1), and (c) a substitute haplotype for haplotype (1), wherein haplotype (1) has a G at the polymorphic sites (PSs) 3 and 4 of the CDK5 gene (SEQ ID NO:1), and wherein polymorphic site (PS) 3 is at nucleotide position 4808 and PS4 is at nucleotide position 5284 of SEQ ID NO:1; and
    assigning the individual to the first galantamine response marker group if the individual has zero copies of any of (a) said haplotype (1), (b) said linked haplotype for haplotype (1), and (c) said substitute haplotype for haplotype (1), assigning the individual to the second galantamine response marker group if the individual has one copy of any of (a) said haplotype (1), (b) said linked haplotype for haplotype (1), and (c) said substitute haplotype for haplotype (1), and assigning the individual to the third galantamine response marker group if the individual has two copies of any of (a) said haplotype (1), (b) said linked haplotype for haplotype (1), and (c) said substitute haplotype for haplotype (1).

15. The method of claim 14, wherein the determining comprises obtaining the individual's genotype for at least one PS in the set of PS that comprise (a) said haplotypes (1); (b) said linked haplotype for haplotypes (1); or (c) said substitute haplotype for haplotype (1).

16. The method of claim 15, wherein the individual's genotype for the set of PSs is obtained by any of (a) a primer extension assay; (b) an allele-specific PCR assay; (c) a nucleic acid amplification assay; (d) a hybridization assay; (e) a mismatch-detection assay; (f) an enzymatic nucleic acid cleavage assay; and (g) a sequencing assay.

17. The method of claim 14, wherein the determining comprises consulting a data repository that provides information on the individual's copy number for any of (a) haplotype (1), (b) a linked haplotype for haplotype (1), or (c) a substitute haplotype for haplotype (1).

18. The method of claim 17, wherein the data repository is the individual's medical records or a medical data card.

19. The method of claim 14, wherein the method comprises:
    determining whether the individual has zero copies, one copy, or two copies of said haplotype (1); and
    assigning the individual to the first galantamine response marker group if the individual has zero copies of haplotype (1), assigning the individual to the second galantamine response marker group if the individual has one copy of haplotype (1), and assigning the individual to the third galantamine response marker group if the individual has two copies of haplotype (1).

20. The method of claim 14, wherein the individual is Caucasian.

21. The method of claim 14, wherein the individual is diagnosed as having a cognitive disorder.

22. The method of claim 14, wherein the individual is a candidate for treatment with a galantamine compound.

23. The method of claim 14, wherein the linkage disequilibrium between the linked haplotype and haplotype (1) has a delta squared value selected from the group consisting of at least 0.75, at least 0.80, at least 0.85, at least 0.90, at least 0.95, and 1.0.

24. The method of claim 23, wherein the linkage disequilibrium between the linked haplotype and haplotype (1) has a delta squared value of at least 0.95.

25. The method of claim 14, wherein the linkage disequilibrium between the allele at a substituting PS in the substitute haplotype and the allele at a substituted PS in haplotype (1) has a delta squared value selected from the group consisting of at least 0.75, at least 0.80, at least 0.85, at least 0.90, at least 0.95, and 1.0.

26. The method of claim 25, wherein the linkage disequilibrium between the allele at a substituting PS and the allele at a substituted PS in haplotype (1) has a delta squared value of at least 0.95.

* * * * *